US012029901B2

(12) United States Patent
Evans et al.

(10) Patent No.: US 12,029,901 B2
(45) Date of Patent: Jul. 9, 2024

(54) DEVICES AND METHODS FOR PREVENTION, MODERATION, AND/OR TREATMENT OF COGNITIVE INJURY

(71) Applicant: Lungpacer Medical Inc., Burnaby (CA)

(72) Inventors: Douglas G. Evans, Downingtown, PA (US); Viral S. Thakkar, Exton, PA (US); Matthew J. Gani, Seattle, WA (US)

(73) Assignee: Lungpacer Medical Inc., Vancouver (CA)

( * ) Notice: Subject to any disclaimer, the term of this patent is extended or adjusted under 35 U.S.C. 154(b) by 614 days.

(21) Appl. No.: 16/022,867

(22) Filed: Jun. 29, 2018

(65) Prior Publication Data

US 2019/0001126 A1 Jan. 3, 2019

Related U.S. Application Data

(60) Provisional application No. 62/527,536, filed on Jun. 30, 2017.

(51) Int. Cl.
*A61N 1/36* (2006.01)
*A61H 31/00* (2006.01)
(Continued)

(52) U.S. Cl.
CPC ........... *A61N 1/3601* (2013.01); *A61H 31/00* (2013.01); *A61N 1/05* (2013.01); *A61N 1/0551* (2013.01);
(Continued)

(58) Field of Classification Search
CPC .. G01R 27/025; G01R 31/2837; G01R 27/08; G16H 20/40; A61N 1/05; A61N 1/0551;
(Continued)

(56) References Cited

U.S. PATENT DOCUMENTS

| 1,693,734 A | 12/1928 | Waggoner |
| 2,532,788 A | 12/1950 | Sarnoff |

(Continued)

FOREIGN PATENT DOCUMENTS

| CN | 1652839 A | 8/2005 |
| CN | 102143781 A | 8/2011 |

(Continued)

OTHER PUBLICATIONS

International Search Report for PCT/US2018/040185, dated Sep. 18, 2018 (7 pages).

(Continued)

*Primary Examiner* — Yingchuan Zhang
*Assistant Examiner* — Sebastian X Lukjan
(74) *Attorney, Agent, or Firm* — Bookoff McAndrews, PLLC

(57) ABSTRACT

This disclosure describes methods and systems for preventing, moderating, and/or treating brain injury. The methods herein may include obtaining a test result reflecting a condition of a brain in the subject, determining a stimulation parameter based on the test result, and stimulating a nerve based on the stimulation parameter, wherein stimulation of the nerve assists or causes contraction of a respiratory muscle in the subject. The systems herein may include a processor configured to: receive a test result reflecting a condition of a brain in a subject, and determine a stimulation parameter based on the test result; and a stimulator configured to stimulate a nerve based on the stimulation parameter, wherein stimulation of the nerve assists or causes contraction of a respiratory muscle in the subject.

23 Claims, 10 Drawing Sheets

(51) Int. Cl.
*A61M 25/01* (2006.01)
*A61N 1/05* (2006.01)
*A61N 5/00* (2006.01)
*A61N 7/00* (2006.01)
*G16H 20/40* (2018.01)

(52) U.S. Cl.
CPC ..... *A61N 1/36014* (2013.01); *A61N 1/36053* (2013.01); *A61N 1/3611* (2013.01); *A61N 1/36135* (2013.01); *A61N 5/00* (2013.01); *A61N 7/00* (2013.01); *G16H 20/40* (2018.01); *A61H 2201/107* (2013.01); *A61H 2201/1253* (2013.01); *A61H 2230/045* (2013.01); *A61H 2230/201* (2013.01); *A61H 2230/405* (2013.01); *A61M 2025/0166* (2013.01); *A61N 2007/0026* (2013.01)

(58) Field of Classification Search
CPC ............ A61N 1/36014; A61N 1/36053; A61N 1/3611; A61N 1/36135; A61N 5/00; A61N 7/00; A61N 1/3601; A61N 2007/0026; A61H 31/00; A61H 2201/107; A61H 2001/1253; A61H 2230/045; A61H 2230/201; A61H 2230/405; A61M 2025/0166
See application file for complete search history.

(56) References Cited

U.S. PATENT DOCUMENTS

| | | |
|---|---|---|
| 2,664,880 A | 1/1954 | Wales, Jr. |
| 3,348,548 A | 10/1967 | Chardack |
| 3,470,876 A | 10/1969 | Barchilon |
| 3,769,984 A | 11/1973 | Muench |
| 3,804,098 A | 4/1974 | Friedman |
| 3,817,241 A | 6/1974 | Grausz |
| 3,835,864 A | 9/1974 | Rasor et al. |
| 3,847,157 A | 11/1974 | Caillouette et al. |
| 3,851,641 A | 12/1974 | Toole et al. |
| 3,896,373 A | 7/1975 | Zelby |
| 3,938,502 A | 2/1976 | Bom |
| 3,983,881 A | 10/1976 | Wickham |
| 4,054,881 A | 10/1977 | Raab |
| 4,072,146 A | 2/1978 | Howes |
| 4,114,601 A | 9/1978 | Abels |
| 4,173,228 A | 11/1979 | Childress et al. |
| 4,249,539 A | 2/1981 | Mezrich et al. |
| 4,317,078 A | 2/1982 | Weed et al. |
| 4,380,237 A | 4/1983 | Newbower |
| 4,407,294 A | 10/1983 | Vilkomerson |
| 4,416,289 A | 11/1983 | Bresler |
| 4,431,005 A | 2/1984 | Mccormick |
| 4,431,006 A | 2/1984 | Trimmer et al. |
| 4,445,501 A | 5/1984 | Bresler |
| RE31,873 E | 4/1985 | Howes |
| 4,573,481 A | 3/1986 | Bullara |
| 4,586,923 A | 5/1986 | Gould et al. |
| 4,587,975 A | 5/1986 | Salo et al. |
| 4,643,201 A | 2/1987 | Stokes |
| 4,674,518 A | 6/1987 | Salo |
| 4,681,117 A | 7/1987 | Brodman et al. |
| 4,683,890 A | 8/1987 | Hewson |
| 4,697,595 A | 10/1987 | Breyer et al. |
| 4,706,681 A | 11/1987 | Breyer et al. |
| 4,771,788 A | 9/1988 | Millar |
| 4,819,662 A | 4/1989 | Heil, Jr. et al. |
| 4,827,935 A | 5/1989 | Geddes et al. |
| 4,830,008 A | 5/1989 | Meer |
| 4,840,182 A | 6/1989 | Carlson |
| 4,852,580 A | 8/1989 | Wood |
| 4,860,769 A | 8/1989 | Fogarty et al. |
| 4,905,698 A | 3/1990 | Strohl, Jr. et al. |
| 4,911,174 A | 3/1990 | Pederson et al. |
| 4,934,049 A | 6/1990 | Kiekhafer et al. |
| 4,944,088 A | 7/1990 | Doan et al. |
| 4,951,682 A | 8/1990 | Petre |
| 4,957,110 A | 9/1990 | Vogel et al. |
| 4,989,617 A | 2/1991 | Memberg et al. |
| 5,005,587 A | 4/1991 | Scott |
| 5,036,848 A | 8/1991 | Hewson |
| 5,042,143 A | 8/1991 | Holleman et al. |
| 5,056,519 A | 10/1991 | Vince |
| 5,115,818 A | 5/1992 | Holleman et al. |
| 5,146,918 A | 9/1992 | Kallok et al. |
| 5,170,802 A | 12/1992 | Mehra |
| 5,184,621 A | 2/1993 | Vogel et al. |
| 5,224,491 A | 7/1993 | Mehra |
| 5,243,995 A | 9/1993 | Maier |
| 5,265,604 A | 11/1993 | Vince |
| 5,267,569 A | 12/1993 | Lienhard |
| 5,314,463 A | 5/1994 | Camps et al. |
| 5,316,009 A | 5/1994 | Yamada |
| 5,324,322 A | 6/1994 | Grill, Jr. et al. |
| 5,330,522 A | 7/1994 | Kreyenhagen |
| 5,335,657 A * | 8/1994 | Terry, Jr. ............... A61B 5/369 607/45 |
| 5,345,936 A | 9/1994 | Pomeranz et al. |
| 5,383,923 A | 1/1995 | Webster, Jr. |
| 5,397,338 A | 3/1995 | Grey et al. |
| 5,411,025 A | 5/1995 | Webster, Jr. |
| 5,417,208 A | 5/1995 | Winkler |
| 5,451,206 A | 9/1995 | Young |
| 5,456,254 A | 10/1995 | Pietroski et al. |
| 5,465,717 A | 11/1995 | Imran et al. |
| 5,476,498 A | 12/1995 | Ayers |
| 5,486,159 A | 1/1996 | Mahurkar |
| 5,507,725 A | 4/1996 | Savage et al. |
| 5,524,632 A | 6/1996 | Stein et al. |
| 5,527,358 A | 6/1996 | Mehmanesh et al. |
| 5,531,686 A | 7/1996 | Lundquist et al. |
| 5,549,655 A | 8/1996 | Erickson |
| 5,555,618 A | 9/1996 | Winkler |
| 5,567,724 A | 10/1996 | Kelleher et al. |
| 5,584,873 A | 12/1996 | Shoberg et al. |
| 5,604,231 A | 2/1997 | Smith et al. |
| 5,665,103 A | 9/1997 | Lafontaine et al. |
| 5,678,535 A | 10/1997 | Dimarco |
| 5,683,370 A | 11/1997 | Luther et al. |
| 5,709,853 A | 1/1998 | Iino et al. |
| 5,716,392 A | 2/1998 | Bourgeois et al. |
| 5,733,255 A | 3/1998 | Dinh et al. |
| 5,755,765 A | 5/1998 | Hyde et al. |
| 5,776,111 A | 7/1998 | Tesio |
| 5,779,732 A | 7/1998 | Amundson |
| 5,782,828 A | 7/1998 | Chen et al. |
| 5,785,706 A | 7/1998 | Bednarek |
| 5,788,681 A | 8/1998 | Weaver et al. |
| 5,813,399 A | 9/1998 | Isaza et al. |
| 5,814,086 A | 9/1998 | Hirschberg et al. |
| RE35,924 E | 10/1998 | Winkler |
| 5,824,027 A | 10/1998 | Hoffer et al. |
| 5,827,192 A | 10/1998 | Gopakumaran et al. |
| 5,916,163 A | 6/1999 | Panescu et al. |
| 5,944,022 A | 8/1999 | Nardella et al. |
| 5,954,761 A | 9/1999 | Machek et al. |
| 5,967,978 A | 10/1999 | Littmann et al. |
| 5,971,933 A | 10/1999 | Gopakumaran et al. |
| 5,983,126 A | 11/1999 | Wittkampf |
| 6,006,134 A | 12/1999 | Hill et al. |
| 6,024,702 A | 2/2000 | Iversen |
| 6,096,728 A | 8/2000 | Collins et al. |
| 6,120,476 A | 9/2000 | Fung et al. |
| 6,123,699 A | 9/2000 | Webster, Jr. |
| 6,126,649 A | 10/2000 | Vantassel et al. |
| 6,136,021 A | 10/2000 | Tockman et al. |
| 6,157,862 A | 12/2000 | Brownlee et al. |
| 6,161,029 A | 12/2000 | Spreigl et al. |
| 6,166,048 A | 12/2000 | Bencherif |
| 6,171,277 B1 | 1/2001 | Ponzi |
| 6,183,463 B1 | 2/2001 | Webster, Jr. |
| 6,198,970 B1 | 3/2001 | Freed et al. |
| 6,198,974 B1 | 3/2001 | Webster, Jr. |

(56) References Cited

U.S. PATENT DOCUMENTS

| | | |
|---|---|---|
| 6,201,994 B1 | 3/2001 | Warman et al. |
| 6,208,881 B1 | 3/2001 | Champeau |
| 6,210,339 B1 | 4/2001 | Kiepen et al. |
| 6,212,435 B1 | 4/2001 | Lattner et al. |
| 6,216,045 B1 | 4/2001 | Black et al. |
| 6,236,892 B1 | 5/2001 | Feler |
| 6,240,320 B1 | 5/2001 | Spehr et al. |
| 6,251,126 B1 | 6/2001 | Ottenhoff et al. |
| 6,269,269 B1 | 7/2001 | Ottenhoff et al. |
| 6,292,695 B1 | 9/2001 | Webster, Jr. et al. |
| 6,295,475 B1 | 9/2001 | Morgan |
| 6,360,740 B1 | 3/2002 | Ward et al. |
| 6,397,108 B1 | 5/2002 | Camps et al. |
| 6,400,976 B1 | 6/2002 | Champeau |
| 6,415,183 B1 | 7/2002 | Scheiner et al. |
| 6,415,187 B1 | 7/2002 | Kuzma et al. |
| 6,438,427 B1 | 8/2002 | Rexhausen et al. |
| 6,445,953 B1 | 9/2002 | Bulkes et al. |
| 6,449,507 B1 | 9/2002 | Hill et al. |
| 6,463,327 B1 | 10/2002 | Lurie et al. |
| 6,493,590 B1 | 12/2002 | Wessman et al. |
| 6,508,802 B1 | 1/2003 | Rosengart et al. |
| 6,526,321 B1 | 2/2003 | Spehr |
| 6,569,114 B2 | 5/2003 | Ponzi et al. |
| 6,584,362 B1 | 6/2003 | Scheiner et al. |
| 6,585,718 B2 | 7/2003 | Hayzelden et al. |
| 6,587,726 B2 | 7/2003 | Lurie et al. |
| 6,602,242 B1 | 8/2003 | Fung et al. |
| 6,610,713 B2 | 8/2003 | Tracey |
| 6,615,085 B1 * | 9/2003 | Boveja ............... A61N 1/36025 607/45 |
| 6,630,611 B1 | 10/2003 | Malowaniec |
| 6,643,552 B2 | 11/2003 | Edell et al. |
| 6,651,652 B1 | 11/2003 | Waard |
| 6,682,526 B1 | 1/2004 | Jones et al. |
| 6,702,780 B1 | 3/2004 | Gilboa et al. |
| 6,718,208 B2 | 4/2004 | Hill et al. |
| 6,721,603 B2 | 4/2004 | Zabara et al. |
| 6,757,970 B1 | 7/2004 | Kuzma et al. |
| 6,778,854 B2 | 8/2004 | Puskas |
| 6,779,257 B2 | 8/2004 | Kiepen et al. |
| 6,844,713 B2 | 1/2005 | Steber et al. |
| RE38,705 E | 2/2005 | Hill et al. |
| 6,881,211 B2 | 4/2005 | Schweikert et al. |
| 6,885,888 B2 | 4/2005 | Rezai |
| 6,907,285 B2 | 6/2005 | Denker et al. |
| 6,934,583 B2 | 8/2005 | Weinberg et al. |
| 6,981,314 B2 | 1/2006 | Black et al. |
| 6,999,820 B2 | 2/2006 | Jordan |
| 7,018,374 B2 | 3/2006 | Schon et al. |
| 7,047,627 B2 | 5/2006 | Black et al. |
| 7,071,194 B2 | 7/2006 | Teng |
| 7,072,720 B2 | 7/2006 | Puskas |
| 7,077,823 B2 | 7/2006 | Mcdaniel |
| 7,082,331 B1 | 7/2006 | Park et al. |
| 7,130,700 B2 | 10/2006 | Gardeski et al. |
| 7,142,903 B2 | 11/2006 | Rodriguez et al. |
| 7,149,585 B2 | 12/2006 | Wessman et al. |
| 7,155,278 B2 | 12/2006 | King et al. |
| 7,167,751 B1 | 1/2007 | Whitehurst et al. |
| 7,168,429 B2 | 1/2007 | Matthews et al. |
| 7,184,829 B2 | 2/2007 | Hill et al. |
| 7,206,636 B1 | 4/2007 | Turcott |
| 7,212,867 B2 | 5/2007 | Van et al. |
| 7,225,016 B1 | 5/2007 | Koh |
| 7,225,019 B2 | 5/2007 | Jahns et al. |
| 7,229,429 B2 | 6/2007 | Martin et al. |
| 7,231,260 B2 | 6/2007 | Wallace et al. |
| 7,235,070 B2 | 6/2007 | Vanney |
| 7,269,459 B1 | 9/2007 | Koh |
| 7,277,757 B2 | 10/2007 | Casavant et al. |
| 7,283,875 B2 | 10/2007 | Larsson et al. |
| 7,340,302 B1 | 3/2008 | Falkenberg et al. |
| 7,363,085 B2 | 4/2008 | Benser et al. |
| 7,363,086 B1 | 4/2008 | Koh et al. |
| 7,371,220 B1 | 5/2008 | Koh et al. |
| 7,416,552 B2 | 8/2008 | Paul et al. |
| 7,421,296 B1 | 9/2008 | Benser et al. |
| 7,454,244 B2 | 11/2008 | Kassab et al. |
| 7,519,425 B2 | 4/2009 | Benser et al. |
| 7,519,426 B1 | 4/2009 | Koh et al. |
| 7,522,953 B2 | 4/2009 | Gharib et al. |
| 7,553,305 B2 | 6/2009 | Honebrink et al. |
| 7,555,349 B2 | 6/2009 | Wessman et al. |
| 7,569,029 B2 | 8/2009 | Clark et al. |
| 7,591,265 B2 | 9/2009 | Lee et al. |
| 7,593,760 B2 | 9/2009 | Rodriguez et al. |
| 7,613,524 B2 | 11/2009 | Jordan |
| 7,636,600 B1 | 12/2009 | Koh |
| 7,670,284 B2 | 3/2010 | Padget et al. |
| 7,672,728 B2 | 3/2010 | Libbus et al. |
| 7,672,729 B2 | 3/2010 | Koh et al. |
| 7,676,275 B1 | 3/2010 | Farazi et al. |
| 7,676,910 B2 | 3/2010 | Kiepen et al. |
| 7,697,984 B2 | 4/2010 | Hill et al. |
| 7,747,323 B2 | 6/2010 | Libbus et al. |
| 7,771,388 B2 | 8/2010 | Olsen et al. |
| 7,783,362 B2 | 8/2010 | Whitehurst et al. |
| 7,794,407 B2 | 9/2010 | Rothenberg |
| 7,797,050 B2 | 9/2010 | Libbus et al. |
| 7,813,805 B1 | 10/2010 | Farazi |
| 7,819,883 B2 | 10/2010 | Westlund et al. |
| 7,840,270 B2 | 11/2010 | Ignagni et al. |
| 7,853,302 B2 | 12/2010 | Rodriguez et al. |
| 7,869,865 B2 | 1/2011 | Govari et al. |
| 7,891,085 B1 | 2/2011 | Kuzma et al. |
| 7,925,352 B2 | 4/2011 | Stack et al. |
| 7,949,409 B2 | 5/2011 | Bly et al. |
| 7,949,412 B1 | 5/2011 | Harrison et al. |
| 7,962,215 B2 | 6/2011 | Ignagni et al. |
| 7,970,475 B2 | 6/2011 | Tehrani et al. |
| 7,972,323 B1 | 7/2011 | Bencini et al. |
| 7,974,693 B2 | 7/2011 | David et al. |
| 7,974,705 B2 | 7/2011 | Zdeblick et al. |
| 7,979,128 B2 | 7/2011 | Tehrani et al. |
| 7,994,655 B2 | 8/2011 | Bauer et al. |
| 8,000,765 B2 | 8/2011 | Rodriguez et al. |
| 8,019,439 B2 | 9/2011 | Kuzma et al. |
| 8,021,327 B2 | 9/2011 | Selkee |
| 8,036,750 B2 | 10/2011 | Caparso et al. |
| 8,050,765 B2 | 11/2011 | Lee et al. |
| 8,052,607 B2 | 11/2011 | Byrd |
| 8,104,470 B2 | 1/2012 | Lee et al. |
| 8,116,872 B2 | 2/2012 | Tehrani et al. |
| 8,121,692 B2 | 2/2012 | Haefner et al. |
| 8,135,471 B2 | 3/2012 | Zhang et al. |
| 8,140,164 B2 | 3/2012 | Tehrani et al. |
| 8,147,486 B2 | 4/2012 | Honour et al. |
| 8,160,701 B2 | 4/2012 | Zhao et al. |
| 8,160,711 B2 | 4/2012 | Tehrani et al. |
| 8,195,297 B2 | 6/2012 | Penner |
| 8,200,336 B2 | 6/2012 | Tehrani et al. |
| 8,206,343 B2 | 6/2012 | Racz |
| 8,224,456 B2 | 7/2012 | Daglow et al. |
| 8,233,987 B2 | 7/2012 | Gelfand et al. |
| 8,233,993 B2 | 7/2012 | Jordan |
| 8,239,037 B2 | 8/2012 | Glenn et al. |
| 8,244,358 B2 | 8/2012 | Tehrani et al. |
| 8,244,359 B2 | 8/2012 | Gelfand et al. |
| 8,244,378 B2 | 8/2012 | Bly et al. |
| 8,255,056 B2 | 8/2012 | Tehrani |
| 8,256,419 B2 | 9/2012 | Sinderby et al. |
| 8,265,736 B2 | 9/2012 | Sathaye et al. |
| 8,265,759 B2 | 9/2012 | Tehrani et al. |
| 8,275,440 B2 | 9/2012 | Rodriguez et al. |
| 8,280,513 B2 | 10/2012 | Tehrani et al. |
| 8,315,713 B2 | 11/2012 | Burnes et al. |
| 8,321,808 B2 | 11/2012 | Goetz et al. |
| 8,335,567 B2 | 12/2012 | Tehrani et al. |
| 8,340,783 B2 | 12/2012 | Sommer et al. |
| 8,348,941 B2 | 1/2013 | Tehrani |
| 8,369,954 B2 | 2/2013 | Stack et al. |
| 8,374,704 B2 | 2/2013 | Desai et al. |
| 8,388,541 B2 | 3/2013 | Messerly et al. |

(56) References Cited

U.S. PATENT DOCUMENTS

| | | |
|---|---|---|
| 8,388,546 B2 | 3/2013 | Rothenberg |
| 8,391,956 B2 | 3/2013 | Zellers et al. |
| 8,401,640 B2 | 3/2013 | Zhao et al. |
| 8,401,651 B2 | 3/2013 | Caparso et al. |
| 8,406,883 B1 | 3/2013 | Barker |
| 8,406,885 B2 | 3/2013 | Ignagni et al. |
| 8,412,331 B2 | 4/2013 | Tehrani et al. |
| 8,412,350 B2 | 4/2013 | Bly |
| 8,428,711 B2 | 4/2013 | Lin et al. |
| 8,428,726 B2 | 4/2013 | Ignagni et al. |
| 8,428,730 B2 | 4/2013 | Stack et al. |
| 8,433,412 B1 | 4/2013 | Westlund et al. |
| 8,442,638 B2 | 5/2013 | Libbus et al. |
| 8,457,764 B2 | 6/2013 | Ramachandran et al. |
| 8,467,876 B2 | 6/2013 | Tehrani |
| 8,473,068 B2 | 6/2013 | Farazi |
| 8,478,412 B2 | 7/2013 | Ignagni et al. |
| 8,478,413 B2 | 7/2013 | Karamanoglu et al. |
| 8,478,426 B2 | 7/2013 | Barker |
| 8,483,834 B2 | 7/2013 | Lee et al. |
| 8,504,158 B2 | 8/2013 | Karamanoglu et al. |
| 8,504,161 B1* | 8/2013 | Kornet ............... A61N 1/36139 607/50 |
| 8,509,901 B2 | 8/2013 | Tehrani |
| 8,509,902 B2 | 8/2013 | Cho et al. |
| 8,509,919 B2 | 8/2013 | Yoo et al. |
| 8,512,256 B2 | 8/2013 | Rothenberg |
| 8,522,779 B2 | 9/2013 | Lee et al. |
| 8,527,036 B2 | 9/2013 | Jalde et al. |
| 8,532,793 B2 | 9/2013 | Morris et al. |
| 8,554,323 B2 | 10/2013 | Haefner et al. |
| 8,560,072 B2 | 10/2013 | Caparso et al. |
| 8,560,086 B2 | 10/2013 | Just et al. |
| 8,571,662 B2 | 10/2013 | Hoffer |
| 8,571,685 B2 | 10/2013 | Daglow et al. |
| 8,615,297 B2 | 12/2013 | Sathaye et al. |
| 8,617,228 B2 | 12/2013 | Wittenberger et al. |
| 8,620,412 B2 | 12/2013 | Griffiths et al. |
| 8,620,450 B2 | 12/2013 | Tockman et al. |
| 8,626,292 B2 | 1/2014 | Mccabe et al. |
| 8,630,707 B2 | 1/2014 | Zhao et al. |
| 8,644,939 B2 | 2/2014 | Wilson et al. |
| 8,644,952 B2 | 2/2014 | Desai et al. |
| 8,646,172 B2 | 2/2014 | Kuzma et al. |
| 8,650,747 B2 | 2/2014 | Kuzma et al. |
| 8,676,323 B2 | 3/2014 | Ignagni et al. |
| 8,676,344 B2 | 3/2014 | Desai et al. |
| 8,694,123 B2 | 4/2014 | Wahlstrand et al. |
| 8,696,656 B2 | 4/2014 | Abboud et al. |
| 8,706,223 B2 | 4/2014 | Zhou et al. |
| 8,706,235 B2 | 4/2014 | Karamanoglu et al. |
| 8,706,236 B2 | 4/2014 | Ignagni et al. |
| 8,718,763 B2 | 5/2014 | Zhou et al. |
| 8,725,259 B2 | 5/2014 | Kornet et al. |
| 8,738,154 B2 | 5/2014 | Zdeblick et al. |
| 8,755,889 B2 | 6/2014 | Scheiner |
| 8,774,907 B2 | 7/2014 | Rothenberg |
| 8,781,578 B2 | 7/2014 | Mccabe et al. |
| 8,781,582 B2 | 7/2014 | Ziegler et al. |
| 8,781,583 B2 | 7/2014 | Cornelussen et al. |
| 8,801,693 B2 | 8/2014 | He et al. |
| 8,805,511 B2 | 8/2014 | Karamanoglu et al. |
| 8,838,245 B2 | 9/2014 | Lin et al. |
| 8,858,455 B2 | 10/2014 | Rothenberg |
| 8,863,742 B2 | 10/2014 | Blomquist et al. |
| 8,886,277 B2 | 11/2014 | Kim et al. |
| 8,897,879 B2 | 11/2014 | Karamanoglu et al. |
| 8,903,507 B2 | 12/2014 | Desai et al. |
| 8,903,509 B2 | 12/2014 | Tockman et al. |
| 8,909,341 B2 | 12/2014 | Gelfand et al. |
| 8,914,113 B2 | 12/2014 | Zhang et al. |
| 8,918,169 B2 | 12/2014 | Kassab et al. |
| 8,918,987 B2 | 12/2014 | Kuzma et al. |
| 8,923,971 B2 | 12/2014 | Haefner et al. |
| 8,942,823 B2 | 1/2015 | Desai et al. |
| 8,942,824 B2 | 1/2015 | Yoo et al. |
| 8,948,884 B2 | 2/2015 | Ramachandran et al. |
| 8,968,299 B2 | 3/2015 | Kauphusman et al. |
| 8,972,015 B2 | 3/2015 | Stack et al. |
| 8,983,602 B2 | 3/2015 | Sathaye et al. |
| 9,008,775 B2 | 4/2015 | Sathaye et al. |
| 9,026,231 B2 | 5/2015 | Hoffer |
| 9,037,264 B2 | 5/2015 | Just et al. |
| 9,042,981 B2 | 5/2015 | Yoo et al. |
| 9,072,864 B2 | 7/2015 | Putz |
| 9,072,899 B1 | 7/2015 | Nickloes |
| 9,108,058 B2 | 8/2015 | Hoffer |
| 9,108,059 B2 | 8/2015 | Hoffer |
| 9,125,578 B2 | 9/2015 | Grunwald |
| 9,138,580 B2 | 9/2015 | Ignagni et al. |
| 9,138,585 B2 | 9/2015 | Saha et al. |
| 9,149,642 B2 | 10/2015 | Mccabe et al. |
| 9,168,377 B2 | 10/2015 | Hoffer |
| 9,199,075 B1* | 12/2015 | Westlund ............... A61N 1/05 |
| 9,205,258 B2 | 12/2015 | Simon et al. |
| 9,216,291 B2 | 12/2015 | Lee et al. |
| 9,220,898 B2 | 12/2015 | Hoffer |
| 9,226,688 B2 | 1/2016 | Jacobsen et al. |
| 9,226,689 B2 | 1/2016 | Jacobsen et al. |
| 9,242,088 B2 | 1/2016 | Thakkar et al. |
| 9,259,573 B2 | 2/2016 | Tehrani et al. |
| 9,295,846 B2 | 3/2016 | Westlund et al. |
| 9,314,618 B2 | 4/2016 | Imran et al. |
| 9,333,363 B2 | 5/2016 | Hoffer et al. |
| 9,345,422 B2 | 5/2016 | Rothenberg |
| 9,370,657 B2 | 6/2016 | Tehrani et al. |
| 9,398,931 B2 | 7/2016 | Wittenberger et al. |
| 9,415,188 B2 | 8/2016 | He et al. |
| 9,427,566 B2 | 8/2016 | Reed et al. |
| 9,427,588 B2 | 8/2016 | Sathaye et al. |
| 9,474,894 B2 | 10/2016 | Mercanzini et al. |
| 9,485,873 B2 | 11/2016 | Shah et al. |
| 9,498,625 B2 | 11/2016 | Bauer et al. |
| 9,498,631 B2 | 11/2016 | Demmer et al. |
| 9,504,837 B2 | 11/2016 | Demmer et al. |
| 9,532,724 B2 | 1/2017 | Grunwald et al. |
| 9,533,160 B2 | 1/2017 | Brooke et al. |
| 9,539,429 B2 | 1/2017 | Brooke et al. |
| 9,545,511 B2 | 1/2017 | Thakkar et al. |
| 9,561,369 B2 | 2/2017 | Burnes et al. |
| 9,566,436 B2 | 2/2017 | Hoffer et al. |
| 9,572,982 B2 | 2/2017 | Burnes et al. |
| 9,597,509 B2 | 3/2017 | Hoffer et al. |
| 9,615,759 B2 | 4/2017 | Hurezan et al. |
| 9,623,252 B2 | 4/2017 | Sathaye et al. |
| 9,662,494 B2 | 5/2017 | Young et al. |
| 9,682,235 B1 | 6/2017 | O'Mahony et al. |
| 9,694,185 B2 | 7/2017 | Bauer |
| 9,717,899 B2 | 8/2017 | Kuzma et al. |
| 9,724,018 B2 | 8/2017 | Cho et al. |
| 9,744,351 B1 | 8/2017 | Gelfand et al. |
| 9,776,005 B2 | 10/2017 | Meyyappan et al. |
| 9,861,817 B2 | 1/2018 | Cho et al. |
| 9,872,989 B2 | 1/2018 | Jung et al. |
| 9,884,178 B2 | 2/2018 | Bouton et al. |
| 9,884,179 B2 | 2/2018 | Bouton et al. |
| 9,919,149 B2 | 3/2018 | Imran et al. |
| 9,931,504 B2 | 4/2018 | Thakkar et al. |
| 9,950,167 B2 | 4/2018 | Hoffer et al. |
| 9,956,396 B2 | 5/2018 | Young et al. |
| 9,968,785 B2 | 5/2018 | Hoffer et al. |
| 9,968,786 B1 | 5/2018 | Bauer et al. |
| 9,987,488 B1* | 6/2018 | Gelfand ............... A61B 5/0826 |
| 2001/0052345 A1 | 12/2001 | Niazi |
| 2002/0026228 A1 | 2/2002 | Schauerte |
| 2002/0056454 A1 | 5/2002 | Samzelius |
| 2002/0065544 A1 | 5/2002 | Smits et al. |
| 2002/0087156 A1 | 7/2002 | Maguire et al. |
| 2002/0128546 A1 | 9/2002 | Silver |
| 2002/0188325 A1 | 12/2002 | Hill et al. |
| 2003/0074039 A1* | 4/2003 | Puskas ............... A61N 1/3686 607/118 |
| 2003/0078623 A1 | 4/2003 | Weinberg et al. |
| 2003/0195571 A1 | 10/2003 | Burnes et al. |

(56) References Cited

U.S. PATENT DOCUMENTS

| | | |
|---|---|---|
| 2004/0003813 A1 | 1/2004 | Banner et al. |
| 2004/0010303 A1 | 1/2004 | Bolea et al. |
| 2004/0030362 A1 | 2/2004 | Hill et al. |
| 2004/0044377 A1 | 3/2004 | Larsson et al. |
| 2004/0064069 A1 | 4/2004 | Reynolds et al. |
| 2004/0077936 A1 | 4/2004 | Larsson et al. |
| 2004/0088015 A1 | 5/2004 | Casavant et al. |
| 2004/0111139 A1 | 6/2004 | Mccreery |
| 2004/0172075 A1 | 9/2004 | Shafer et al. |
| 2004/0186543 A1 | 9/2004 | King et al. |
| 2004/0210261 A1 | 10/2004 | King et al. |
| 2005/0004565 A1 | 1/2005 | Vanney |
| 2005/0013879 A1 | 1/2005 | Lin et al. |
| 2005/0021102 A1 | 1/2005 | Ignagni et al. |
| 2005/0027338 A1 | 2/2005 | Hill |
| 2005/0033136 A1 | 2/2005 | Govari et al. |
| 2005/0033137 A1 | 2/2005 | Oral et al. |
| 2005/0043765 A1 | 2/2005 | Williams et al. |
| 2005/0065567 A1 | 3/2005 | Lee et al. |
| 2005/0070981 A1 | 3/2005 | Verma |
| 2005/0075578 A1 | 4/2005 | Gharib et al. |
| 2005/0085865 A1 | 4/2005 | Tehrani |
| 2005/0085866 A1 | 4/2005 | Tehrani |
| 2005/0085867 A1 | 4/2005 | Tehrani et al. |
| 2005/0085868 A1 | 4/2005 | Tehrani et al. |
| 2005/0085869 A1 | 4/2005 | Tehrani et al. |
| 2005/0096710 A1 | 5/2005 | Kieval |
| 2005/0109340 A1 | 5/2005 | Tehrani |
| 2005/0113710 A1 | 5/2005 | Stahmann et al. |
| 2005/0115561 A1 | 6/2005 | Stahmann et al. |
| 2005/0131485 A1 | 6/2005 | Knudson et al. |
| 2005/0138791 A1 | 6/2005 | Black et al. |
| 2005/0138792 A1 | 6/2005 | Black et al. |
| 2005/0143787 A1 | 6/2005 | Boveja et al. |
| 2005/0165457 A1 | 7/2005 | Benser et al. |
| 2005/0182454 A1 | 8/2005 | Gharib et al. |
| 2005/0187584 A1 | 8/2005 | Denker et al. |
| 2005/0192655 A1 | 9/2005 | Black et al. |
| 2005/0251238 A1 | 11/2005 | Wallace et al. |
| 2005/0251239 A1 | 11/2005 | Wallace et al. |
| 2005/0288728 A1 | 12/2005 | Libbus et al. |
| 2005/0288730 A1 | 12/2005 | Deem et al. |
| 2006/0030894 A1 | 2/2006 | Tehrani |
| 2006/0035849 A1 | 2/2006 | Spiegelman et al. |
| 2006/0058852 A1 | 3/2006 | Koh et al. |
| 2006/0074449 A1 | 4/2006 | Denker et al. |
| 2006/0079936 A1 | 4/2006 | Boveja et al. |
| 2006/0122661 A1 | 6/2006 | Mandell |
| 2006/0122662 A1 | 6/2006 | Tehrani et al. |
| 2006/0130833 A1 | 6/2006 | Younes |
| 2006/0142815 A1 | 6/2006 | Tehrani et al. |
| 2006/0149334 A1 | 7/2006 | Tehrani et al. |
| 2006/0155222 A1 | 7/2006 | Sherman et al. |
| 2006/0167523 A1 | 7/2006 | Tehrani et al. |
| 2006/0188325 A1 | 8/2006 | Dolan |
| 2006/0195159 A1 | 8/2006 | Bradley et al. |
| 2006/0217791 A1 | 9/2006 | Spinka et al. |
| 2006/0224209 A1 | 10/2006 | Meyer |
| 2006/0229677 A1 | 10/2006 | Moffitt et al. |
| 2006/0247729 A1 | 11/2006 | Tehrani et al. |
| 2006/0253161 A1 | 11/2006 | Libbus et al. |
| 2006/0253182 A1 | 11/2006 | King |
| 2006/0258667 A1 | 11/2006 | Teng |
| 2006/0259107 A1 | 11/2006 | Caparso et al. |
| 2006/0282131 A1 | 12/2006 | Caparso et al. |
| 2006/0287679 A1 | 12/2006 | Stone |
| 2007/0005053 A1 | 1/2007 | Dando |
| 2007/0021795 A1 | 1/2007 | Tehrani |
| 2007/0027448 A1 | 2/2007 | Paul et al. |
| 2007/0043400 A1 | 2/2007 | Donders et al. |
| 2007/0087314 A1 | 4/2007 | Gomo |
| 2007/0093875 A1 | 4/2007 | Chavan et al. |
| 2007/0106339 A1 | 5/2007 | Errico et al. |
| 2007/0106357 A1 | 5/2007 | Denker et al. |
| 2007/0112402 A1 | 5/2007 | Grill et al. |
| 2007/0112403 A1 | 5/2007 | Moffitt et al. |
| 2007/0118183 A1 | 5/2007 | Gelfand et al. |
| 2007/0150006 A1 | 6/2007 | Libbus et al. |
| 2007/0150026 A1 | 6/2007 | Bourget et al. |
| 2007/0168007 A1 | 7/2007 | Kuzma et al. |
| 2007/0173900 A1 | 7/2007 | Siegel et al. |
| 2007/0191908 A1 | 8/2007 | Jacob et al. |
| 2007/0196780 A1 | 8/2007 | Ware et al. |
| 2007/0203549 A1 | 8/2007 | Demarais et al. |
| 2007/0208388 A1 | 9/2007 | Jahns et al. |
| 2007/0221224 A1 | 9/2007 | Pittman et al. |
| 2007/0240718 A1 | 10/2007 | Daly |
| 2007/0250056 A1 | 10/2007 | Vanney |
| 2007/0250162 A1 | 10/2007 | Royalty |
| 2007/0255379 A1 | 11/2007 | Williams et al. |
| 2007/0265611 A1 | 11/2007 | Ignagni et al. |
| 2007/0288076 A1 | 12/2007 | Bulkes et al. |
| 2008/0039916 A1 | 2/2008 | Colliou et al. |
| 2008/0065002 A1 | 3/2008 | Lobl et al. |
| 2008/0125828 A1 | 5/2008 | Ignagni et al. |
| 2008/0161878 A1 | 7/2008 | Tehrani et al. |
| 2008/0167695 A1 | 7/2008 | Tehrani et al. |
| 2008/0177190 A1 | 7/2008 | Libbus et al. |
| 2008/0177347 A1 | 7/2008 | Tehrani et al. |
| 2008/0183186 A1 | 7/2008 | Bly et al. |
| 2008/0183187 A1 | 7/2008 | Bly |
| 2008/0183239 A1 | 7/2008 | Tehrani et al. |
| 2008/0183240 A1 | 7/2008 | Tehrani et al. |
| 2008/0183253 A1 | 7/2008 | Bly |
| 2008/0183254 A1 | 7/2008 | Bly et al. |
| 2008/0183255 A1 | 7/2008 | Bly et al. |
| 2008/0183259 A1 | 7/2008 | Bly et al. |
| 2008/0183264 A1 | 7/2008 | Bly et al. |
| 2008/0183265 A1 | 7/2008 | Bly et al. |
| 2008/0188903 A1 | 8/2008 | Tehrani et al. |
| 2008/0215106 A1 | 9/2008 | Lee et al. |
| 2008/0288010 A1 | 11/2008 | Tehrani et al. |
| 2008/0288015 A1 | 11/2008 | Tehrani et al. |
| 2008/0312712 A1 | 12/2008 | Penner |
| 2008/0312725 A1 | 12/2008 | Penner |
| 2009/0024047 A1 | 1/2009 | Shipley et al. |
| 2009/0024176 A1* | 1/2009 | Yun ............ A61N 1/3627 607/20 |
| 2009/0036947 A1 | 2/2009 | Westlund et al. |
| 2009/0118785 A1 | 5/2009 | Ignagni et al. |
| 2009/0275956 A1 | 11/2009 | Burnes et al. |
| 2009/0275996 A1 | 11/2009 | Burnes et al. |
| 2009/0276022 A1 | 11/2009 | Burnes et al. |
| 2010/0022950 A1 | 1/2010 | Anderson et al. |
| 2010/0036451 A1* | 2/2010 | Hoffer ............ A61N 1/36185 607/42 |
| 2010/0057046 A1 | 3/2010 | Stevens (Webber) et al. |
| 2010/0077606 A1 | 4/2010 | Black et al. |
| 2010/0094376 A1* | 4/2010 | Penner ............ A61N 1/0517 607/42 |
| 2010/0105977 A1* | 4/2010 | De Taboada ........ A61N 5/0622 600/9 |
| 2010/0114227 A1 | 5/2010 | Cholette |
| 2010/0114254 A1 | 5/2010 | Kornet |
| 2010/0198296 A1 | 8/2010 | Ignagni et al. |
| 2010/0204766 A1 | 8/2010 | Zdeblick et al. |
| 2010/0268311 A1 | 10/2010 | Cardinal et al. |
| 2010/0312302 A1 | 12/2010 | Zealear |
| 2010/0319691 A1 | 12/2010 | Lurie et al. |
| 2011/0060380 A1 | 3/2011 | Gelfand et al. |
| 2011/0060381 A1 | 3/2011 | Ignagni et al. |
| 2011/0077726 A1 | 3/2011 | Westlund et al. |
| 2011/0087301 A1 | 4/2011 | Li et al. |
| 2011/0118815 A1 | 5/2011 | Kuzma et al. |
| 2011/0152967 A1 | 6/2011 | Bruce et al. |
| 2011/0190845 A1 | 8/2011 | Weisfeldt et al. |
| 2011/0224750 A1* | 9/2011 | Scheiner ............ A61N 1/36114 607/17 |
| 2011/0230932 A1 | 9/2011 | Tehrani et al. |
| 2011/0230935 A1 | 9/2011 | Zdeblick |
| 2011/0230945 A1 | 9/2011 | Ohtaka et al. |
| 2011/0270358 A1 | 11/2011 | Davis et al. |
| 2011/0288609 A1 | 11/2011 | Tehrani et al. |
| 2012/0035684 A1 | 2/2012 | Thompson et al. |

(56) References Cited

U.S. PATENT DOCUMENTS

| | | |
|---|---|---|
| 2012/0053654 A1 | 3/2012 | Tehrani et al. |
| 2012/0078320 A1 | 3/2012 | Schotzko et al. |
| 2012/0130217 A1 | 5/2012 | Kauphusman et al. |
| 2012/0158091 A1 | 6/2012 | Tehrani et al. |
| 2012/0209284 A1 | 8/2012 | Westlund et al. |
| 2012/0215278 A1 | 8/2012 | Penner |
| 2012/0323293 A1 | 12/2012 | Tehrani et al. |
| 2013/0018247 A1 | 1/2013 | Glenn et al. |
| 2013/0018427 A1 | 1/2013 | Pham et al. |
| 2013/0023972 A1 | 1/2013 | Kuzma et al. |
| 2013/0030496 A1 | 1/2013 | Karamanoglu et al. |
| 2013/0030497 A1 | 1/2013 | Karamanoglu et al. |
| 2013/0030498 A1 | 1/2013 | Karamanoglu et al. |
| 2013/0060245 A1 | 3/2013 | Grunewald et al. |
| 2013/0066392 A1 | 3/2013 | Bruce et al. |
| 2013/0116743 A1 | 5/2013 | Karamanoglu et al. |
| 2013/0123891 A1 | 5/2013 | Swanson |
| 2013/0131743 A1 | 5/2013 | Yamasaki et al. |
| 2013/0150908 A1 | 6/2013 | Lindenthaler |
| 2013/0158625 A1 | 6/2013 | Gelfand et al. |
| 2013/0165989 A1 | 6/2013 | Gelfand et al. |
| 2013/0167372 A1 | 7/2013 | Black et al. |
| 2013/0197601 A1 | 8/2013 | Tehrani et al. |
| 2013/0237906 A1 | 9/2013 | Park et al. |
| 2013/0268018 A1 | 10/2013 | Brooke et al. |
| 2013/0289686 A1 | 10/2013 | Masson et al. |
| 2013/0296964 A1 | 11/2013 | Tehrani |
| 2013/0296973 A1 | 11/2013 | Tehrani et al. |
| 2013/0317580 A1* | 11/2013 | Simon .............. A61N 2/006 607/115 |
| 2013/0317587 A1 | 11/2013 | Barker |
| 2013/0333696 A1 | 12/2013 | Lee et al. |
| 2014/0067032 A1 | 3/2014 | Morris et al. |
| 2014/0088580 A1 | 3/2014 | Wittenberger et al. |
| 2014/0114371 A1 | 4/2014 | Westlund et al. |
| 2014/0121716 A1 | 5/2014 | Casavant et al. |
| 2014/0128953 A1 | 5/2014 | Zhao et al. |
| 2014/0148780 A1 | 5/2014 | Putz |
| 2014/0288551 A1 | 9/2014 | Rupinder et al. |
| 2014/0316486 A1 | 10/2014 | Zhou et al. |
| 2014/0324115 A1 | 10/2014 | Ziegler et al. |
| 2014/0378803 A1 | 12/2014 | Geistert et al. |
| 2015/0018839 A1 | 1/2015 | Morris et al. |
| 2015/0034081 A1 | 2/2015 | Tehrani et al. |
| 2015/0045810 A1 | 2/2015 | Hoffer et al. |
| 2015/0045848 A1 | 2/2015 | Cho et al. |
| 2015/0119950 A1 | 4/2015 | Demmer et al. |
| 2015/0142082 A1* | 5/2015 | Simon ............ A61N 1/36132 607/61 |
| 2015/0165207 A1 | 6/2015 | Karamanoglu |
| 2015/0196354 A1 | 7/2015 | Haverkost et al. |
| 2015/0196356 A1 | 7/2015 | Kauphusman et al. |
| 2015/0231348 A1 | 8/2015 | Lee et al. |
| 2015/0250982 A1 | 9/2015 | Osypka et al. |
| 2015/0265833 A1 | 9/2015 | Meyyappan et al. |
| 2015/0283340 A1 | 10/2015 | Zhang et al. |
| 2015/0290476 A1 | 10/2015 | Krocak et al. |
| 2015/0359487 A1 | 12/2015 | Coulombe |
| 2015/0374252 A1 | 12/2015 | De et al. |
| 2015/0374991 A1 | 12/2015 | Morris et al. |
| 2016/0001072 A1 | 1/2016 | Gelfand et al. |
| 2016/0114165 A1* | 4/2016 | Levine ............ A61N 1/36146 607/116 |
| 2016/0144078 A1 | 5/2016 | Young et al. |
| 2016/0193460 A1 | 7/2016 | Xu et al. |
| 2016/0228696 A1 | 8/2016 | Imran et al. |
| 2016/0239627 A1 | 8/2016 | Cerny et al. |
| 2016/0256692 A1* | 9/2016 | Baru .............. A61N 1/36514 |
| 2016/0287877 A1 | 10/2016 | Jung |
| 2016/0310730 A1 | 10/2016 | Martins et al. |
| 2016/0331326 A1 | 11/2016 | Xiang et al. |
| 2016/0367815 A1 | 12/2016 | Hoffer |
| 2017/0007825 A1 | 1/2017 | Thakkar et al. |
| 2017/0013713 A1 | 1/2017 | Shah et al. |
| 2017/0021166 A1 | 1/2017 | Bauer et al. |
| 2017/0028191 A1 | 2/2017 | Mercanzini et al. |
| 2017/0036017 A1 | 2/2017 | Tehrani et al. |
| 2017/0050033 A1 | 2/2017 | Wechter |
| 2017/0143973 A1 | 5/2017 | Tehrani |
| 2017/0143975 A1 | 5/2017 | Hoffer et al. |
| 2017/0196503 A1 | 7/2017 | Narayan et al. |
| 2017/0224993 A1 | 8/2017 | Sathaye et al. |
| 2017/0232250 A1 | 8/2017 | Kim et al. |
| 2017/0252558 A1 | 9/2017 | O'Mahony et al. |
| 2017/0291023 A1 | 10/2017 | Kuzma et al. |
| 2017/0296812 A1 | 10/2017 | O'Mahony et al. |
| 2017/0312006 A1 | 11/2017 | Mcfarlin et al. |
| 2017/0312507 A1 | 11/2017 | Bauer et al. |
| 2017/0312508 A1 | 11/2017 | Bauer et al. |
| 2017/0312509 A1 | 11/2017 | Bauer et al. |
| 2017/0326359 A1 | 11/2017 | Gelfand et al. |
| 2017/0347921 A1 | 12/2017 | Haber et al. |
| 2018/0001086 A1 | 1/2018 | Bartholomew et al. |
| 2018/0008821 A1 | 1/2018 | Gonzalez et al. |
| 2018/0110562 A1 | 4/2018 | Govari et al. |
| 2018/0117334 A1 | 5/2018 | Jung |
| 2018/0280691 A1 | 10/2018 | Ackermann et al. |

FOREIGN PATENT DOCUMENTS

| | | |
|---|---|---|
| EP | 0993840 A1 | 4/2000 |
| EP | 1304135 A2 | 4/2003 |
| EP | 0605796 B1 | 8/2003 |
| EP | 1833558 A1 | 9/2007 |
| EP | 1833558 B1 | 5/2011 |
| EP | 2489395 A1 | 8/2012 |
| FR | 2801509 A1 | 6/2001 |
| JP | 108510677 A | 11/1996 |
| JP | 2003503119 A | 1/2003 |
| JP | 2010516353 A | 5/2010 |
| JP | 2011200571 A | 10/2011 |
| JP | 2012000195 A | 1/2012 |
| WO | 9407564 A2 | 4/1994 |
| WO | 9508357 A1 | 3/1995 |
| WO | 9964105 A1 | 12/1999 |
| WO | 9965561 A1 | 12/1999 |
| WO | 0100273 A1 | 1/2001 |
| WO | 02058785 A1 | 8/2002 |
| WO | 03094855 A1 | 11/2003 |
| WO | 2005053788 A1 | 6/2005 |
| WO | 2006066280 A1 | 6/2006 |
| WO | 2006110338 A1 | 10/2006 |
| WO | 2006115877 A1 | 11/2006 |
| WO | 2007053508 A1 | 5/2007 |
| WO | 2008092246 A1 | 8/2008 |
| WO | 2008094344 A1 | 8/2008 |
| WO | 2009006337 A1 | 1/2009 |
| WO | 2009134459 A2 | 11/2009 |
| WO | 2010029842 A1 | 3/2010 |
| WO | 2010148412 A1 | 12/2010 |
| WO | 2011158410 A1 | 12/2011 |
| WO | 2012106533 A2 | 8/2012 |
| WO | 2013131187 A1 | 9/2013 |
| WO | 2013188965 A1 | 12/2013 |

OTHER PUBLICATIONS

Escher, Doris J.W. et al., "Clinical Control of Respiration by Transvenous Phrenic Pacing," American Society for Artificial Internal Organs: Apr. 1968—vol. 14—Issue 1—pp. 192-197.

Ishii, K. et al., "Effects of Bilateral Transvenous Diaphragm Pacing on Hemodynamic Function in Patients after Cardiac Operations," J. Thorac. Cardiovasc. Surg., 1990.

Antonica A., et al., "Vagal Control of Lymphocyte Release from Rat Thymus," Journal of the Autonomic Nervous System, Elsevier, vol. 48(3), Aug. 1994, pp. 187-197.

Ayas N.T., et al., "Prevention of Human Diaphragm Atrophy with Short periods of Electrical Stimulation," American Journal of Respiratory and Critical Care Medicine, Jun. 1999, vol. 159(6), pp. 2018-2020.

Borovikova, et al., "Role of the Vagus Nerve in the Anti-Inflammatory Effects of CNI-1493," Proceedings of the Annual

(56) References Cited

OTHER PUBLICATIONS

Meeting of Professional Research Scientists: Experimental Biology 2000, Abstract 97.9, Apr. 15-18, 2000.
Borovikovaa L.V., et al., "Role of Vagus Nerve Signaling in CNI-1493—Mediated Suppression of Acute Inflammation," Autonomic Neuroscience: Basic and Clinical, vol. 85 (1-3), Dec. 20, 2000, pp. 141-147.
Borovikovaa L.V., et al., "Vagus Nerve Stimulation Attenuates the Systemic Inflammatory Response to Endotoxin," Nature, Macmillan Magazines Ltd, vol. 405, May 25, 2000, pp. 458-462.
Chinese Search Report for Application No. CN2013/80023357.5, dated Jul. 24, 2015.
Co-pending U.S. Appl. No. 15/606,867, filed May 26, 2017.
Daggeti, W.M. et al., "Intracaval Electrophrenic Stimulation. I. Experimental Application during Barbiturate Intoxication Hemorrhage and Gang," Journal of Thoracic and Cardiovascular Surgery, 1966, vol. 51 (5), pp. 676-884.
Daggeti, W.M. et al., "Intracaval electrophrenic stimulation. II. Studies on Pulmonary Mechanics Surface Tension Urine Flow and Bilateral Ph," Journal of Thoracic and Cardiovascular Surgery, 1970, vol. 60(1 ), pp. 98-107.
De Gregorio, M.A. et al., "The Gunther Tulip Retrievable Filter: Prolonged Temporary Filtration by Repositioning within the Inferior Vena Cava," Journal of Vascular and Interventional Radiology, 2003, vol. 14, pp. 1259-1265.
Deng Y-J et al., "The Effect of Positive Pressure Ventilation Combined with Diaphragm Pacing on Respiratory Mechanics in Patients with Respiratory Failure; Respiratory Mechanics," Chinese critical care medicine, Apr. 2011, vol. 23(4), pp. 213-215.
European Search Report for U.S. Appl. No. 13/758,363, dated Nov. 12, 2015.
European Search Report for Application No. EP17169051.4, dated Sep. 8, 2017, 7 pages.
Extended European Search Report for Application No. 14864542.7, dated Jun. 2, 2017, 8 pages.
Extended European Search Report for Application No. 15740415.3, dated Jul. 7, 2017.
Fleshner M., et al., "Thermogenic and Corticosterone Responses to Intravenous Cytokines (IL-1$\beta$ and TNF-$\alpha$) are Attenuated by Subdiaphragmatic Vagotomy," Journal of Neuroimmunology, vol. 86, Jun. 1998, pp. 134-141.
Frisch S., "A Feasibility Study of a Novel Minimally Invasive Approach for Diaphragm Pacing," Master of Science Thesis, Simon Fraser University, 2009, p. 148.
Furman, S., "Transvenous Stimulation of the Phrenic Nerves," Journal of Thoracic and Cardiovascular Surgery, 1971, vol. 62 (5), pp. 743-751.
Gaykema R.P.A. et al., "Subdiaphragmatic Vagotomy Suppresses Endotoxin-Induced Activation of Hypothalamic Corticotropin-Releasing Hormone Neurons and ACTH Secretion," Endocrinology, The Endocrine Society, vol. 136 (10), 1995, pp. 4717-4720.
Gupta A.K., "Respiration Rate Measurement Based on Impedance Pneumography," Data Acquisition Products, Texas Instruments, Application Report, SBAA181, Feb. 2011, 11 pages.
Guslandi M., "Nicotine Treatment for Ulcerative Colitis," The British Journal of Clinical Pharmacology, Blackwell Science Ltd, vol. 48, 1999, pp. 481-484.
Hoffer J.A. et al., "Diaphragm Pacing with Endovascular Electrodes", IFESS 2010—International Functional Electrical Stimulation Society, 15th Anniversary Conference, Vienna, Austria, Sep. 2010.
Japanese Office Action in corresponding Japanese Application No. 2014-560202, dated Dec. 6, 2016, 4 pages.
Japanese Office Action in corresponding Japanese Application No. 2014-560202, dated Oct. 17, 2017, 5 pages.
Kawashima K., et al., "Extraneuronal Cholinergic System in Lymphocytes," Pharmacology & Therapeutics, Elsevier, vol. 86, 2000, pp. 29-48.

Levine S., et al., "Rapid disuse atrophy of diaphragm fibers in mechanically ventilated humans," New England Journal of Medicine, 2008, vol. 358, pp. 1327-1335.
Lungpacer: Therapy, News . . . Accessed Dec. 27, 2016.
Madretsma, G.S., et al., "Nicotine Inhibits the In-vitro Production of Interleukin 2 and Tumour Necrosis Factor-$\alpha$ by Human Mononuclear Cells," Immunopharmacology, Elsevier, vol. 35 (1), Oct. 1996, pp. 47-51.
Marcy, T.W. et al., "Diaphragm Pacing for Ventilatory Insufficiency," Journal of Intensive Care Medicine, 1987, vol. 2 (6), pp. 345-353.
Meyyappan R., "Diaphragm Pacing during Controlled Mechanical Ventilation: Pre-Clinical Observations Reveal a Substantial Improvement in Respiratory Mechanics", 17th Biennial Canadian Biomechanics Society Meeting, Burnaby, BC, Jun. 6-9, 2012.
Nabutovsky, Y., et al., "Lead Design and Initial Applications of a New Lead for Long-Term Endovascular Vagal Stimulation," Pace, Blackwell Publishing, Inc, vol. 30(1), Jan. 2007, pp. S215-S218.
Notification of Reasons for Rejection and English language translation issued in corresponding Japanese Patent Application No. 2015-517565, dated Mar. 28, 2017, 6 pages.
Onders R.,, "A Diaphragm Pacing as a Short-Term Assist to Positive Pressure Mechanical Ventilation in Critical Care Patients," Chest, Oct. 24, 2007, vol. 132(4), pp. 5715-5728.
Onders R.,, "Diaphragm Pacing for Acute Respiratory Failure," Difficult Decisions in Thoracic Surgery, Chapter 37, Springer-Verlag, 2011, M.K. Ferguson (ed.), pp. 329-335.
Onders R, et al., "Diaphragm Pacing with Natural Orifice Transluminal Endoscopic Surgery: Potential for Difficult-To-Wean Intensive Care Unit Patients," Surgical Endoscopy, 2007, vol. 21, pp. 475-479.
Pavlovic D., et al., "Diaphragm Pacing During Prolonged Mechanical Ventilation of the Lungs could Prevent from Respiratory Muscle Fatigue," Medical Hypotheses, vol. 60 (3), 2003, pp. 398-403.
Planas R.F., et al., "Diaphragmatic Pressures: Transvenous vs. Direct Phrenic Nerve Stimulation," Journal of Applied Physiology, vol. 59(1), 1985, pp. 269-273.
Romanovsky, A.A., et al., "The Vagus Nerve in the Thermoregulatory Response to Systemic Inflammation," American Journal of Physiology, vol. 273 (1 Pt 2), 1997, pp. R407-R413.
Salmela L., et al., "Verification of the Position of a Central Venous Catheter by Intra-Atrial ECG. When does this method fail?," Acta Anasthesiol Scand, vol. 37 (1), 1993, pp. 26-28.
Sandborn W.J., "Transdermal Nicotine for Mildly to Moderately Active Ulcerative Colitis," Annals of Internal Medicine, vol. 126 (5), Mar. 1, 1997, pp. 364-371.
Sandoval R., "A Catch/Ike Property-Based Stimulation Protocol for Diaphragm Pacing", Master of Science Coursework project, Simon Fraser University, Mar. 2013.
Sarnoff, S.J. et al., "Electrophrenic Respiration," Science, 1948, vol. 108, p. 482.
Sato E., et al., "Acetylcholine Stimulates Alveolar Macrophages to Release Inflammatory Cell Chemotactic Activity," American Journal of Physiology, vol. 274 (Lung Cellular and Molecular Physiology 18), 1998, pp. L970-L979.
Sato, K.Z., et al., "Diversity of mRNA Expression for Muscarinic Acetylcholine Receptor Subtypes and Neuronal Nicotinic Acetylcholine Receptor Subunits in Human Mononuclear Leukocytes and Leukemic Cell Lines," Neuroscience Letters, vol. 266 (1), 1999, pp. 17-20.
Schauerte P., et al., "Transvenous Parasympathetic Nerve Stimulation in the Inferior Vena Cava and Atrioventricular Conduction," Journal of Cardiovascular Electrophysiology, vol. 11 (1), Jan. 2000, pp. 64-69.
Schauerte P.N., et al., "Transvenous Parasympathetic Cardiac Nerve Stimulation: An Approach for Stable Sinus Rate Control," Journal of Cardiovascular Electrophysiology, vol. 10 (11), Nov. 1999, pp. 1517-1524.
Scheinman R.I., et al., "Role of Transcriptional Activation of I$\kappa$B$\alpha$ in Mediation of Immunosuppression by Glucocorticoids," Science, vol. 270, Oct. 13, 1995, pp. 283-286.
Sher, M.E., et al., "The Influence of Cigarette Smoking on Cytokine Levels in Patients with Inflammatory Bowel Disease," Inflammatory Bowel Diseases, vol. 5 (2), May 1999, pp. 73-78.

(56) References Cited

OTHER PUBLICATIONS

Steinlein, O., "New Functions for Nicotinic Acetylcholine Receptors?," Behavioural Brain Research, vol. 95, 1998, pp. 31-35.
Sternberg E.M., (Series Editor) "Neural-Immune Interactions in Health and Disease," The Journal of Clinical Investigation, vol. 100 (11), Dec. 1997, pp. 2641-2647.
Sykes., A.P., et al., "An Investigation into the Effect and Mechanisms of Action of Nicotine in Inflammatory Bowel Disease," Inflammation Research, vol. 49, 2000, pp. 311-319.
Toyabe S., et al., "Identification of Nicotinic Acetylcholine Receptors on Lymphocytes in the Periphery as well as Thymus in Mice," Immunology, vol. 92, 1997, pp. 201-205.
Van Dijk A.P.M., et al., "Transdermal Nicotine Inhibits Interleukin 2 Synthesis by Mononuclear Cells Derived from Healthy Volunteers," European Journal of Clinical Investigation, vol. 28, 1998, pp. 664-671.
Wanner, A. et al., "Trasvenous Phrenic Nerve Stimulation in Anesthetized Dogs," Journal of Applied Physiology, 1973, vol. 34 (4), pp. 489-494.
Watkins L.R., et al., "Blockade of Interleukin-1 Induced Hyperthermia by Subdiaphragmatic Vagotomy: Evidence for Vagal Mediation of Immune-Brain Communication," Neuroscience Letters, vol. 183, 1995, pp. 27-31.
Watkins L.R., et al., "Implications of Immune-to-Brain Communication for Sickness and Pain," PNAS (Proceedings of the National Academy of Sciences of the USA), vol. 96 (14), Jul. 6, 1999, pp. 7710-7713.
Whaley K., et al., "C2 Synthesis by Human Monocytes is Modulated by a Nicotinic Cholinergic Receptor," Nature, vol. 293, Oct. 15, 1981, pp. 580-582 (and reference page).

\* cited by examiner

DEVICES AND METHODS FOR PREVENTION, MODERATION, AND/OR TREATMENT OF COGNITIVE INJURY

CROSS-REFERENCE

This application claims priority to U.S. Provisional Application No. 62/527,536, filed on Jun. 30, 2017, the entire disclosure of which is hereby incorporated by reference in its entirety.

In general, all publications, patent applications, and patents mentioned in this specification are herein incorporated by reference in their entirety to the same extent as if each individual document was specifically individually indicated to be incorporated by reference.

TECHNICAL FIELD

The embodiments of this disclosure generally relate to methods, systems, and devices for the diagnosis, mitigations, and treatment of cognitive injury (e.g. mechanical ventilation induced delirium, stroke, concussion, etc.). In some examples, the present disclosure is directed to a method of reducing the occurrence of brain cell damage or death in a subject. One exemplary aspect is directed to a method of reducing the occurrence of brain cell damage or death caused by transient cerebral hypoxia/ischemia condition, brain inflammation condition, or a traumatic brain injury (TBI) event. Another exemplary aspect is directed to devices, systems, and methods for reducing brain and/or cognitive injury in patients on mechanical ventilation. Yet another exemplary aspect is directed to mitigating diaphragm muscle, lung, and brain injury.

BACKGROUND

Critical care patients, particularly those requiring invasive mechanical ventilation (MV), often experience higher levels of diaphragm, lung, brain, and other organ injury. The diaphragm muscle may rapidly lose muscle mass and strength. The lungs may suffer from ventilator-induced trauma. Cognitive effects may be caused by several factors including aberrant neuro-signaling and inflammatory responses. Patients presenting with existing cognitive injury such as, for example, from a traumatic (e.g. concussion) or ischemic (e.g. stroke) brain event may be at an even greater risk for rapid cognitive deterioration once placed on MV. There remains a need for cost-effective, practical, surgically simple and minimally invasive apparatus and methods that may reduce diaphragm, lung, and cognitive injury (e.g. delirium, dementia, and cognitive dysfunction, etc.) in ICU patients, particularly for those patients on MV.

During natural breathing, the diaphragm and other respiratory muscles contract to create a region of negative pressure outside the lungs. The lungs expand to equalize pressure, and air naturally flows into the lungs. When air is flowing into the lungs, this is inhalation, the act of breathing in. Most mechanical ventilators help patients breathe by assisting the inhalation of oxygen into the lungs and the exhalation of carbon dioxide by using positive pressure to periodically pressurize and/or inflate the lungs. While lifesaving in many respects, MV may also be detrimental.

For example, MV may induce Ventilator Induced Lung Injury (VILI), including, for example, volutrauma, atelectrauma, and biotrauma. Volutrauma is damage from overdistension of the lung parenchyma, which may result from high tidal volume and/or low lung compliance. Atelectrauma may result from recruitment-decruitment of collapsed alveoli during each ventilator cycle, generally a result of low tidal volume (Vt), low pressure, or inadequate levels of Positive End Expiratory Pressure (PEEP). Biotrauma is the expression of a local inflammatory process and may be characterized by the release of inflammatory mediators because of over-distending tidal volumes and repetitive opening and closing of unstable lung units.

Lung injury may lead to the activation of inflammatory genes and the release of inflammatory mediators from cells in the lungs. Cyclic stretch (CS) of the lung tissue may cause inflammatory cell infiltration, which may contribute to loss of capillary-alveolar barrier function, increased expression of pro-inflammatory mediators, including tumor necrosis factor-$\alpha$ and IL-6, and induction of cellular apoptosis. As free inflammatory mediators originating from the lungs circulate through the organs of the body, the free inflammatory mediators may impair oxygen delivery and may lead to organ failure. MV may contribute to compartmentalization of lung inflammatory response leading to multiple organ dysfunction syndromes. Thus, MV induced stress and strain in the lungs may result in inflammatory response of the alveoli, recruitment of neutrophils to lung parenchyma, and the production of cytokines. This process may then spread into intravascular circulation systems, and may reach distal organs, such as, for example, the brain.

Further, the lungs may sense the MV induced mechanical stimuli by mechanoreceptors, and the lung may communicate this information to the brain, via the autonomic nervous system. The diaphragm has significant sensory innervations.

Generally, the goals of mechanical ventilation are to provide precise control of the respiratory variables, such as, for example, partial pressure of arterial oxygen ($PaO_2$) and partial pressure of arterial carbon dioxide ($PaCO_2$) control. The mechanical ventilator may cyclically pressurize the lungs to provide effective gas exchange. It is important to balance goals with minimizing lung stretch and minimizing lower lung collapse. The unique lung volume, lung compliance, and gas exchange requirements for each patient may complicate these goals.

Decreased tidal volumes may lead to hypercapnia (increased $PaCO_2$). Hypercapnia may lead to intracranial hypertension. Improved systemic oxygenation may reduce brain hypoxic insults. However, excessively high ventilator pressures may lead to systemic inflammatory response, which, in turn, may affect cerebral oxygenation and metabolism, thereby inducing brain injury.

PEEP may be used to recruit previously collapsed alveoli, improve arterial oxygenation, and reduce elastance of the respiratory system. However, PEEP may be detrimental to gas exchange, decrease cardiac output by reducing aortic blood flow/pressure, and may lead to barotrauma.

Protective mechanical ventilation with moderate to lower tidal volumes (e.g. 6 mL/kg), limiting plateau pressure <30 cm $H_2O$, and utilizing PEEP of 10 cm $H_2O$ versus higher Vt and no PEEP may lead to less lung inflammation and reduce mortality. However, a single ventilation approach likely does not fit all scenarios. Even for a single patient, it may be difficult to balance diaphragm protection, lung protection, and brain protection, and provide adequate gas exchange for the patient. As such, clinicians may be forced to use balanced approaches, making tradeoffs and accepting potential injury to one organ while reducing the likelihood of injury to another organ.

Thus, there remains a need to limit or reverse lung injury for mechanically ventilated patients.

Although MV can be a life-saving intervention for patients suffering from respiratory failure, prolonged MV can promote diaphragmatic atrophy and contractile dysfunction (VIDD). This type of diaphragm injury and the accompanying diaphragm weakness may contribute to difficulty in weaning from MV.

The majority of patients treated with MV are readily liberated from ventilator support upon resolution of respiratory failure or recovery from surgery, but approximately one-third of patients encounter challenges with regaining the ability to breathe spontaneously. The prognosis may be favorable for patients who wean from MV successfully at the first attempt, but is less so for the remaining patients.

To date, there remains an unmet need to limit or reverse the diaphragm injury for mechanically ventilated patients.

The diaphragm muscle is an important crossroad for information involving the entire body. In addition to serving as the primary respiratory muscle, it has links throughout the body as part of an information network necessary for breathing. The diaphragm has significant sensory innervations. Both the phrenic and vagus nerves are part of this network, and each nerve contains both sensory and motor fibers. As an example, the vagus nerve which innervates the crural region of the diaphragm, can directly affect the system of reciprocal tension membranes (e.g. dura), producing a range of relevant symptoms in the body. In a similar mechanism, the event of diaphragmatic dysfunction can lead to a cascade of signaling events, which affect the brain and other organs. As both vagus and phrenic nerves innervate the diaphragm muscle, stimulation of either the vagus or phrenic nerve can affect a signaling cascade in the other. The potential implications of the stimuli on the brain, other body organs, and tissues will be discussed further below.

Both delirium and cognitive dysfunction occur in as many as 87% of the intensive care unit (ICU) patients when they are provided with pulmonary support via invasive MV (Ely E W et al., "Delirium in mechanically ventilated patients: validity and reliability of the confusion assessment method for the intensive care unit (CAM-ICU)," JAMA, 2001). While treatment methods have progressed, delirium and cognitive dysfunction remain a major problem in MV patients.

Aberrant neuro-signaling may lead to neurological, cellular, and inflammatory processes, which may lead to cognitive impairment during and after treatment with mechanical ventilation.

A vagotomy in subjects receiving MV may mitigate the increase in the levels of the dopamine-synthesizing enzyme and the degree of apoptosis in the hippocampus compared to control animals. This implies that the vagus nerve is sending a signal, related to MV, to cause the dopamine increase.

Critical care patients with a preexisting brain injury (e.g., stroke, TBI, acute ischemia, etc.), who are placed on mechanical ventilation, are at an increased risk for long term cognitive defects. Thus, there is a need for preventative or neuroprotective therapy that is efficacious in humans.

Inflammation is a common pathomechanism of acute lung injury and acute brain injury, affecting brain homeostasis. The inflammatory cascade following an acute brain injury may adversely affect the lungs, but evidence indicates that the opposite can occur as well. This can occur by means of a complex interaction between the autonomic, neuro-inflammatory, neuroendocrine, and immunologic pathways, which are physiologically programmed to preserve systemic homeostasis, but in certain circumstances may be responsible for harmful effects on remote organs and systems.

The lungs sense mechanical stimuli via mechanoreceptors, and the information is communicated to the brain via the autonomic nervous system. The afferent vagal nerves communicate information from pulmonary stretch receptors to the respiratory center in the brain. To date, there remains a need for effective treatments to help treat or mitigate both brain and lung injuries.

Afferent and efferent vagus nerves, α7 nAChR-expressing inflammatory cells, and central vagal nucleus in the brain form an inflammatory reflex that may control inflammation and immunity. Sensory neurons detect pathogens, damage, or injury via peripheral afferent vagal nerve endings and may then provide feedback to nucleus tractus solitarii (NTS) in the brain stem. The information is processed, and the efferent vagus nerve may transmit integrated information by action potentials to the celiac ganglion and then to other parts of the body.

The vagus nerve originates from medullar oblongata, which consists of four nuclei: dorsal nucleus, nucleus ambiguous, NTS, and spinal nucleus of trigeminal nerve. Approximately 80% of afferent sensory fibers are contained in the vagus nerve and are responsible for transmission of the information to the NTS. There are numerous afferent vagus nerve endings in the lungs and diaphragm. For example, lung information is transmitted via the afferent arm to NTS, a processing center, which is capable of differentiating types of infection, inflammation, or injury. The vagal nerve endings may synthesize and release Ach, which in turn activates α7 nAChR in the pro-inflammatory cells such as macrophages and neutrophils or epithelial cells to regulate the production of pro-inflammatory cytokines via NF-κB.

One mechanism for the transient ischemia protection involves the afferent vagal pathway. The vagus nerve consists of both afferent and efferent fibers with 80% of the afferent impulses originating in the thoracic and abdominal organs. The afferent activity is relayed to the NTS, which has projections to the locus coeruleus (LC) which controls the release of norepinephrine (NE) and 5-hydroxytryptamine (5-HT). NE activated by VNS may have anti-inflammatory effects and may stimulate the release of 5-HT. Data showing that agonists of 5-HT may reduce the release of glutamate in cerebral ischemia indicating the 5-HT attenuates excitotoxicity by inhibiting glutamate release. These afferent nerve pathway effects could contribute to the effectiveness of NVS in brain ischemia. Alternatively, the efferent vagal pathway may also induce neuroprotection via the cholinergic anti-inflammatory pathway (CAP) which is activated by the central cholinergic system in the brain via the efferent fiber of the vagus nerve.

Electrical stimulation of the vagus nerve leading to the activation of the CAP may suppress brain inflammation, leading to neuroprotection in ischemic stroke. The efferent vagus nerve stimulation can also inhibit a localized inflammatory cytokine cascade in tissues and organs that are served by efferent vagus nerve fibers.

When activated, the resident macrophages of the central nervous system (CNS), the microglia, may secrete molecules that cause neuronal dysfunction, or degeneration. It has further been discovered that stimulation of efferent vagus nerve fibers releases sufficient acetylcholine to mitigate a systemic inflammatory cytokine cascade, as occurs in endotoxic shock, or a localized inflammatory cytokine cascade.

Vagus nerve stimulation may cause up-regulation (expression) of α7 nAChR. The cellular and molecular mechanism for anti-inflammation may be partly attributable to acetylcholine (Ach), a neurotransmitter mainly released from vagus nerve endings. Activation of α7 nAChR by Ach on macrophages may suppress the release of pro-inflammatory cytokines in peripheral circulation, thereby preventing tissue damage via the inflammation reflex of the VN. The α7 nAChR receptors are commonly expressed in the brain including neurons glia and endothelial cells. Activation of these receptors may enhance neuronal resistance to ischemic or other types of insults.

An alternate technique to stimulate neural tissue, without the need for invasive procedures, is temporally interfering stimulation and involves crossing two high frequency electrical signals at the specific brain region to be stimulated. The two signals interfere with each other, resulting in a low frequency signal at the target area. Low frequency signals may provoke neurons to fire, while high frequency signals do not, so the targeted area may be activated while the surrounding tissue is not.

SUMMARY

Embodiments of the present disclosure relate to, among other things, systems, devices, and methods for preventing, moderating, and/or treating brain injury. Each of the embodiments disclosed herein may include one or more of the features described in connection with any of the other disclosed embodiments.

This disclosure includes methods for treating a subject. In some aspects, the methods may include obtaining a test result reflecting a condition of a brain in the subject; determining a stimulation parameter based on the test result; and stimulating a nerve based on the stimulation parameter, wherein stimulation of the nerve assists or causes contraction of a respiratory muscle in the subject. In some examples, the nerve may be a phrenic nerve, and the respiratory muscle may be a diaphragm muscle.

In some examples, the nerve may be a first nerve, and the methods may further include stimulating a second nerve, wherein stimulation of the second nerve initiates a biological response in the brain that reduces a level of a causing factor of a brain injury. The second nerve may be a vagus nerve. The stimulation of the second nerve may affect signaling from the second nerve to the brain or a lung in the subject. The methods may further include stimulating a third nerve. In these cases, the second nerve may be a left vagus nerve, and the third nerve may be a right vagus nerve. In some cases, the nerve may be a first nerve, and the methods may further include inhibiting transmission of an aberrant signal by a second nerve.

In some examples, the second nerve may be stimulated by a nerve stimulator. For example, the second nerve may be stimulated by an external nerve stimulator. The external nerve stimulator may be positioned on a skin area adjacent to a vagus nerve in the subject. Alternatively or additionally, the second nerve may be stimulated by an implantable nerve stimulator. The second nerve may be stimulated by manual, mechanical, electrical, ultrasonic, or electromagnetic energy.

In some examples, the test result may be from imaging the brain. Alternatively or additionally, the test result may comprise a level of an inflammation- or pain-related protein in blood of the subject. The methods may further include performing a test that provides the test result.

In some examples, stimulating the nerve may include inserting a catheter with one or more electrodes in a blood vessel of the subject, and positioning the one or more electrodes proximate the nerve.

In some examples, the methods may further include ventilating the subject with a mechanical ventilator. In such cases, the test result may comprise an effect of ventilation on the brain. The methods may further include stimulating a second nerve during at least a portion of a ventilation inspiration period.

In some aspects, the methods of treating a subject may include stimulating a first nerve with a first stimulator to assist or cause contraction of a respiratory muscle in the subject; and stimulating a second nerve with the first stimulator or a second stimulator to reduce a level of a causing factor of a brain injury. The methods may further include stimulating a third nerve with the first stimulator, the second stimulator, or a third stimulator to assist or cause contraction of the respiratory muscle in the subject. The causing factor of the brain injury may be inflammation in the brain. The first nerve may be a phrenic nerve, and the second nerve may be a vagus nerve. The respiratory muscle may be a diaphragm muscle.

In some examples, the stimulation of the first nerve may be in synchrony with stimulation of the third nerve. Alternatively or additionally, the stimulation of the first nerve may be coordinated with stimulation of the second nerve. The stimulation of the first nerve may be in synchrony with stimulation of the second nerve.

In some examples, the methods may further include ventilating the subject with a mechanical ventilator. The second nerve may be stimulated during at least a portion of a ventilation inspiration period.

In some example, the stimulation of the second nerve may be performed while the first nerve is not stimulated by the first stimulator. The first stimulator may comprise an intravascular catheter having a set of electrodes configured to stimulate a phrenic nerve. The second stimulator may comprise an intravascular catheter having a set of electrodes configured to stimulate a vagus nerve.

In some aspects, the methods for treating a subject may include stimulating a first nerve with a stimulator to assist or cause contraction of a respiratory muscle in the subject; obtaining a test result of a vagus nerve activity in the subject; generating a stimulation parameter based on test result; and stimulating at least one of the first nerve and a second nerve based on the stimulation parameter. The second nerve may be a vagus nerve, and stimulating at least one of the first nerve and the second nerve based on the stimulation parameter may include stimulating the second nerve based on the stimulation parameter. The first nerve may be a first phrenic nerve, and the second nerve may be a second phrenic nerve. In some cases, the test result may be obtained by testing heart blood flow, testing peripheral blood flow, testing blood pressure, imaging, or assessing inflammation- or pain-related molecules in blood of the subject.

The disclosure also includes systems. In some aspects, the systems may include a processor configured to: receive a test result reflecting a condition of a brain in a subject; and determine a stimulation parameter based on the test result; and a stimulator configured to stimulate a nerve based on the stimulation parameter, wherein stimulation of the nerve assists or causes contraction of a respiratory muscle in the subject. The systems may further include a mechanical ventilator. The systems may further include one or more switches operatively connected to the processor, the one or more switches being configured to regulate stimulation output to the stimulator.

In some examples, the systems may further include a sensor configured to detect a cardiac event, a respiratory event, a catheter location, a blood pressure, or a level of an inflammatory agent. The stimulator may be in communication with the sensor. The stimulator may comprise an intravascular catheter having a first set of electrodes configured to stimulate a right phrenic nerve and a second set of electrodes configured to stimulate a left phrenic nerve. The stimulator may be configured to affect signaling of a phrenic nerve, signaling of a vagus nerve, or a combination thereof.

In some aspects, the systems may include an electrode configured to stimulate a first nerve to assist or cause contraction of a respiratory muscle in the subject; and a stimulator configured to stimulate a second nerve to reduce a level of a causing factor of a brain injury. The stimulator may comprise an intravascular catheter having one or ore electrodes configured to stimulate a vagus nerve. The systems may further include a catheter configured for intravascular insertion, wherein the catheter comprises a first plurality of electrodes and a second plurality of electrodes.

In some aspects, the systems may include a first nerve stimulator configured to stimulate a first nerve, wherein stimulation of the first nerve assists or causes contraction of a respiratory muscle in the subject; and a processor configured to: receive a test result of a vagus nerve activity in the subject, and generate a stimulation parameter based on the test result; and a second nerve stimulator configured to stimulate a second nerve based on the stimulation parameter.

BRIEF DESCRIPTION OF DRAWINGS

The accompanying drawings, which are incorporated in and constitute a part of this specification, illustrate non-limiting embodiments of the present disclosure and together with the description serve to explain the principles of the disclosure.

DETAILED DESCRIPTION

Figure 1:
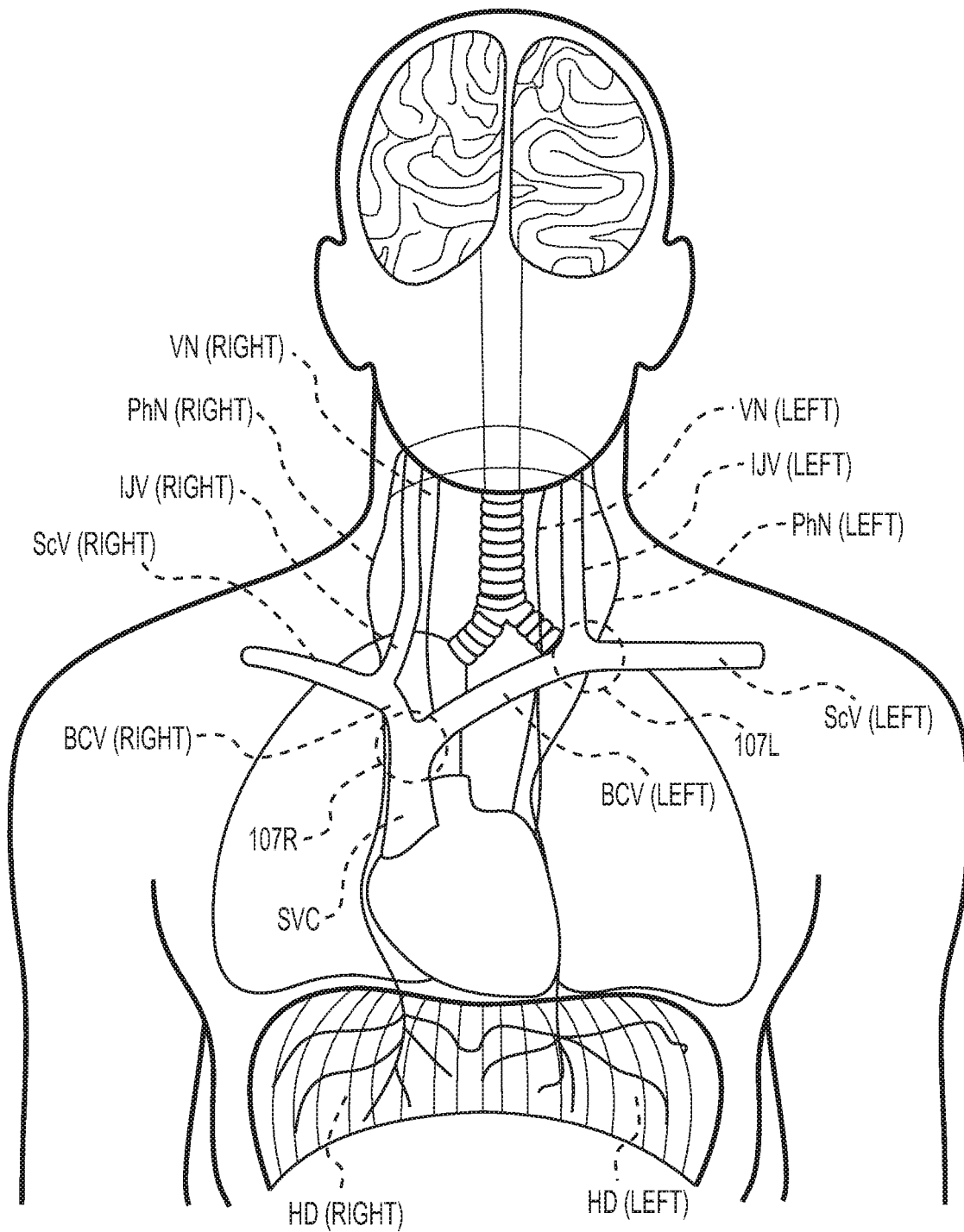
FIG. 1 illustrates the anatomy of selected nerves, tissues, and blood vessels in a person's neck, brain, lungs, and upper torso.

Throughout the following description, specific details are set forth to provide a more thorough understanding to persons skilled in the art. The following description of examples of the technology is not intended to be exhaustive or to limit the system to the precise forms of any example embodiment. Accordingly, the description and drawings are to be regarded in an illustrative, rather than a restrictive, sense.

Further aspects of the disclosures and features of example embodiments are illustrated in the appended drawings and/or described in the text of this specification and/or described in the accompanying claims. It may be understood that both the foregoing general description and the following detailed description are exemplary and explanatory only and are not restrictive of the invention, as claimed. As used herein, the terms "comprises," "comprising," "including," "having," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−15% of a stated value.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the body or closer to an operator using the medical device or insertion device. In contrast, "distal" refers to a position relatively further away from the operator using the medical device or insertion device, or closer to the interior of the body.

In general, embodiments of this disclosure relate to systems, medical devices, and methods for electrically stimulating a patient's nerves, and preventing, modulating, controlling, or treating injury (e.g., injury of the brain, the lungs, or the diaphragm muscle). For example, the injury may be caused or enhanced by mechanical ventilation. As used herein, the term "injury" may refer to an alteration in cellular or molecular integrity, activity, level, robustness, state, or other alteration that is traceable to an event. For example, brain injury may be neuronal injury resulting from stress (repetitive stress), inflammation, oxidative stress, disease, pain, stroke, and/or physical injury such as surgery or trauma.

The methods herein may include stimulating one or more nerves, such as one or more phrenic nerves and/or one or more vagus nerves. For example, the methods may include stimulating one or more respiratory muscles (e.g., diaphragm muscle) or a portion thereof by stimulating one or more nerves (e.g., phrenic nerves). Stimulation of one or more phrenic nerves may play a role in preventing or treating brain injury (e.g., caused by mechanical ventilation). For example, in patients receiving mechanical ventilation, stimulation of phrenic nerves may pace the diaphragm muscle so that the pressure and time required from the mechanical ventilation are reduced. Alternatively or additionally, stimulation of phrenic nerves may initiate a response in the brain to reduce a causing factor of brain injury, such as inflammation. Stimulation of one or more vagus nerves may also initiate a response in the brain to reduce a causing factor of brain injury, such as inflammation. In some cases, the method may include blocking one or more vagus nerves so that the vagus nerve(s) does not transmit aberrant signals (e.g., signals that trigger inflammation in the brain) to the brain. The aberrant signals may result from mechanical ventilation.

The methods may further include monitoring, sensing, and/or testing one or more functions, activity, or other parameters of the brain, obtaining the results of the sensing or tests, and analyzing these results, for example, to determine the effect of the nerve stimulation and/or mechanical ventilation on brain function and/or activity. Based on the test results and their analysis, parameters (e.g., timing, duration, and profile such as intensity) for nerve stimulation may be generated or modified, and stimulation of nerves may be initiated or modified based on the parameters. Exemplary tests on brain function include magnetic resonance imaging (MRI) such as functional MRI, a computed tomography (CAT) scan, a positron emission tomography (PET) scan, a magnetoencephalography (MEG) scan, any other imaging or scanning modality, an electroencephalogram (EEG) test, detection of a cardiac event and/or a respiratory event, and/or measurement of blood pressure, intracranial pressure, cardiopulmonary pressure, brain oxygenation, and partial pressure of carbon dioxide in arterial blood ($PaCO_2$). Brain oxygenation may be monitored in several ways including via jugular venous saturation, near-infrared spectroscopy, and/or microdialysis catheter assessment. Tests on brain function may also include laboratory tests of one or more bodily fluids (e.g., blood, urine, fluid surrounding the brain, etc.), or one or more tissues. The laboratory tests may detect levels of molecules (e.g., cytokines) indicative of brain injury or dysfunction, such as inflammation. Tests on brain function may further include neurological examinations (e.g., assessing of motor or sensory skills, like testing reflexes, eye movements, walking, and balance), and tissue biopsy. The tests may further include cognitive assessment (e.g., assessing mental status) by asking patients to conduct specific tasks and answer several questions, such as naming today's date or following a written instruction.

Alternatively or additionally, the methods may include testing the status of one or more nerve (e.g., vagus nerve) stimulations. In some cases, the methods may include testing brain function and the status of one or more nerve stimulations. Exemplary tests on the status of nerve (e.g., vagus nerve) stimulations include detection of electrodermal activity, heart rate variability, responses related to the control of pupil diameter and blood flow to the eye, peripheral blood flow (e.g., measured with laser Doppler flow meters), heart rate and blood pressure variability analysis, valsalva maneuver, deep metronomic breathing, a sustained handgrip test, a cold pressor test, a cold face test, active and passive orthostatic challenge maneuvers, blood pressure response to a mental arithmetic test, pharmacological baroreflex testing, a thermoregulatory sweat test, a quantitative sudomotor axon reflex test, magnetic resonance imaging (MRI), single-photon emission computed tomography (SPECT), evaluation of electroencephalography (EEG) waveforms, the measurement of visual, audio and somatosensory evoked potentials, changes in absolute vital sign values, and changes in pain threshold. The tests may also include detecting chemistry (e.g., levels and activities of proteins or other molecules such as inflammation- or pain-related molecules) in the blood or other bodily fluids. The chemistry tests may include measuring the level and/concentrations of TNF-$\alpha$, other cytokines, serotonin, gastrin, and/or norepinephrine.

The tests on brain function and/or vagus nerve stimulation may be performed prior to, during, or after ventilation or at different stages of ventilation. For example, the tests may be performed before, during, or after an inflation stage of mechanical ventilation. Alternatively or additionally, the tests may be performed before, during, or after stimulation of a nerve. Brain function and/or vagus nerve stimulation status or activity may be determined based on the test results. Alternatively or additionally, the results from the tests performed at different times may be compared to each other or to reference threshold values or ranges, e.g. thresholds or ranges that indicate normal brain function or other levels of brain function. In such cases, brain function and/or vagus nerve stimulation status may be determined based on the comparisons.

For a patient receiving or having received a nerve stimulation therapy, the brain function and/or vagus nerve stimulation status in the patient may be detected and compared to parameters indicative of normal function and/or status of the brain and/or the nerves. If a difference is determined, one or more parameters of nerve stimulation may be modified to adjust the nerve stimulation therapy administered to the patient. The adjustment may be performed continuously (e.g., based on real-time monitoring of brain function and/or vagus nerve stimulation status) for delivering optimal and personalized therapy to the patient.

In some cases, the methods may further include administering one or more drugs to the subject during the nerve stimulation, pacing, and/or ventilation procedure described herein. In embodiments, the drug therapy may be based on the analysis of any of the tests described above. In some cases, the one or more drugs may include those associated with decreased time to extubation and helpful in reducing brain injury. For example, the one or more drugs may include propofol and/or dexmedetomidine. In some cases, the one or more drugs may include those affecting smooth muscle tension and/or capable of reducing trachea-bronchial tone/tension. Such drugs may also help reduce pulmonary stretch receptor-induced aberrant vagus signaling responsible for brain injury.

The systems herein may include medical devices for performing the methods described in the disclosure. The medical device may include components such as a catheter having a tubular member and one or more electrode assemblies, a signal generator to provide stimulation energy to the electrode assemblies, one or more sensors to sense the condition of the patient and adjust the stimulation signals, and one or more control components allowing a user (e.g., a physician or a patient) to adjust the parameters of nerve stimulation. The different embodiments of the various medical device components may be combined and used together in any logical arrangement. Furthermore, individual features or elements of any described embodiment may be combined with or used in connection with the individual features or elements of other embodiments. The various embodiments may further be used in different contexts than those specifically described herein. For example, the disclosed electrode structures may be combined or used in combination with various deployment systems known in the art for various diagnostic and/or therapeutic applications.

The systems and methods disclosed in this disclosure may help to achieve at least one or more of the following to a patient: preventing, modulating, controlling, or treating brain injury, preventing, modulating, controlling, or treating lung injury, activating the diaphragm muscle (e.g., by stimulating phrenic nerves), or providing respiratory support or mechanical ventilation.

In some embodiments, the systems and methods herein may reduce and prevent brain injury (e.g., in patients receiving or have received mechanical ventilation) via phrenic or diaphragm stimulation. Electrical stimulation of at least one phrenic nerve and/or hemi-diaphragm during mechanical ventilation may provide effective $O_2/CO_2$ gas exchange while reducing upper lung barotrauma (stretch injury) and reducing atelectasis (lung collapse injury). Reducing lung injury may reduce the stimulus that leads to a cascade of events linked to brain inflammation and cognitive dysfunction. Electrical stimulation of one or more phrenic nerves or diaphragm muscle may result in stabilizing the afferent signaling to the brain to mitigate aberrant vagal signaling implicated in brain cell death. The diaphragm muscle activation by phrenic or other nerve/muscle stimulation may provide improved or stabilizing sensory input to brain receptors, compared to those sent during mechanical ventilation alone (e.g. thereby replacing the input typically received by the brain, as non-limiting examples from phrenic, vagus, or pulmonary stretch receptor signaling, during brain-driven diaphragm activation). The period of stimulation may vary since biological structures may prefer slight variation. The stimulation (e.g. phrenic, vagus, muscle, etc.) may be provided by a transvascular (e.g., transvenous) catheter, cuff electrodes, implanted electrodes, transcutaneous stimulators, or other suitable methods. For example, stimulation of vagus nerves may be provided by an external nerve stimulator, e.g., a stimulator positioned on a skin area adjacent to a vagus nerve. Alternatively or additionally, stimulation of vagus nerves may be provided by an implantable nerve stimulator.

In some embodiments, the systems and methods herein may reduce brain injury via vagus nerve block coordinated with mechanical ventilation-delivered breath. Electrical stimulation may be used to block the aberrant pain signals, e.g., by using a kilohertz frequency nerve block via vagus nerves, which may reduce inactivation of Akt (protein kinase B) and help mitigate cell death. Kilohertz frequency electrical stimulation could be delivered (e.g. at or about 40 kHz, or within a range of [1 kHz-100 kHz]) via electrodes placed on or near the vagus nerve (e.g., including a branch of the vagus nerve) to temporarily block afferent signals. The blocking signal may be designed to occur in synchrony with a specific phase (e.g., inspiration) of the mechanically delivered breath to minimize aberrant signaling. The blocking signal may be designed such that its intensity is modulated by one or more characteristics of the mechanical ventilation delivered breath (e.g., pressure, flow, tidal volume). The vagus-blocking signal may be delivered via transcutaneous electrodes, minimally invasively placed electrodes, transvenous electrodes, subcutaneous electrodes, direct contact electrodes, or other suitable delivery vehicle. The stimulation profile envelope of the blocking signal may be tailored to minimize the passage of the aberrant vagus signaling to the brain caused, for example, by the pulmonary stretch pain receptors. In one embodiment, the systems may include a sensor for adjusting the timing, duration, and profile of the nerve block signal to optimize the blockade of the aberrant signal. Sensors or other inputs may be used to trigger the blocking signal. For example, in one embodiment, the detection of breaths (e.g. coming from the mechanical ventilator) may be used to coordinate/synchronize stimulation of the phrenic nerve(s) and/or stimulation of the vagus nerve(s) with the mechanical ventilator. One such sensor includes a mechanical transducer placed on the patient's neck or throat (e.g. a microphone) that can detect the "pink noise" in the throat or endotracheal tube whenever a breath occurs. Alternatively, in another embodiment, a transducer may be attached in the airflow circuit (e.g. the inspiratory limb, where the inspiratory phase of the breath could be detected) or inserted or attached to a portion of the airflow circuit tubing. This may be used with an invasive or a non-invasive mechanical ventilator. In yet another embodiment, a mechanical transducer on a portion of the airflow circuit (e.g. a strain gauge) may serve as a stretch-detector that is clipped or wrapped around the tubing (either the inspiratory limb, or the tube that connects the wye-piece to the endotracheal tube). Changes in pressure associated with the breathing cycle may be detected by the mechanical transducer to synchronize stimulation.

In some embodiments, methods and systems herein may reduce diaphragm, lung, and brain injury via phrenic stimulation, and vagus nerve block coordinated with MV delivered breath. Stimulating at least one phrenic nerve may activate the diaphragm, which may stabilize aberrant signals sent to the brain via afferent neuro pathways, mitigating diaphragm atrophy, and reducing lung injury. The activation of diaphragm may also include stimulating at least one vagus nerve to block a signal. In one aspect, both left and right phrenic and vagus nerves may be stimulated. These stimulation signals may be delivered by one or more devices. A single catheter placed via the left (Internal Jugular) IJ or (External Jugular) EJ may stimulate the left vagus, left phrenic, and right phrenic nerve. In one aspect, an electrode population for sending the left vagus nerve block may be located proximal to the other electrode populations. In such an embodiment, the block may not prevent the distal phrenic signals from reaching the diaphragm muscle. The therapies may also be delivered by two or more separate devices. For example, an intravenous catheter placed in the jugular vein (internal or external) or subclavian vein may be used in combination with an external vagus stimulation device mounted on a neck collar, skin mounted transcutaneous device, or a set of electrodes placed percutaneously. The vagus nerve block may be timed to occur with the delivery of the mechanical ventilation breath, or with delivery of the phrenic nerve stimulation. A variety of sensors may be used to coordinate the stimulation with a patient's breathing or with the delivery of a breath from the mechanical ventilator. Sensors may sense heart rate, $CO_2$, $O_2$, breathing, temperature, motion, impedance, electromyography, electrocardiography, airflow, pressure, or any combination thereof.

In some embodiments, the methods and systems herein may reduce diaphragm injury, lung injury, and/or brain injury via phrenic stimulation, and/or vagus stimulation, and in some cases vagus nerve block coordinated with mechanical ventilation delivered breath. Electrical stimulation may also be used to deliver anti-inflammatory signaling via the vagus nerve. Low duty cycle signaling may be effective in providing long-term cerebral protection. In one embodiment, positive vagus pulse trains may be sent in between phrenic stimulation pulses. Alternatively or additionally, blocking pulses to the vagus nerve may be sent between positive stimulation pulses to the vagus nerve, or at the same time, or with portions of overlap. For example, positive (passivating) signals may be sent to the brain via the vagus nerve during the time between breaths, and the nerve block on the vagus nerve may be established when the mechanical ventilator is stretching the lungs to block the pain signal from reaching the brain. The blocking signal may be designed such that its intensity is modulated by one or more characteristics of the mechanical ventilation delivered breath (e.g., pressure, flow, tidal volume, etc.). The positive signal to the vagus may be designed such that its intensity is modulated by one or more characteristics of the mechanical ventilation delivered breath (e.g., inversely proportional to pressure, flow, tidal volume, etc.). In some cases, vagus nerve stimulation immediately after an ischemic event may be neuroprotective. For example, a patient may receive a pulse train delivered to a vagus nerve after a cerebral ischemic event. The pulse train may be interrupted to establish a nerve block when the ventilator is inflating the lungs, then the positive signal may be re-initiated between breaths. Alternatively or additionally, the positive signal may be sent continuously and it may be blocked by high frequency nerve block (e.g., every few seconds). In some cases, the positive signal does not have to been sent all the time or for long periods of time. For example, the positive signal may be sent once every few hours, or once a day.

Vagus stimulation may be transvascular, transdermal, or via minimally invasive electrodes placed in the proximity of the vagus nerve. Techniques may include selectively activating and/or blocking efferent and afferent neural pathways. This may involve simultaneous afferent vagus blocking and efferent phrenic stimulation. Another aspect includes a vagus stimulation device that delivers a nerve block during the inspiration phase of mechanical ventilation and then an anti-inflammatory stimulation signal to the vagus nerve at other time periods (e.g., a jugular catheter for vagus stimulation that synchronizes with the mechanical ventilation or with the phrenic nerve stimulation signal, delivering high frequency block when stretch receptors are activated and delivering anti-inflammation inducing signals other times).

In some embodiments, the methods and systems herein may reduce brain injury via phrenic pacing in mechanical ventilation patients. Aspects of the present disclosure may include systems and methods for reducing peak ventilator pressure, limiting end-inspiratory lung stretch to provide adequate ventilation while reducing lung inflammation, and reducing atelectrauma.

In some embodiments, the methods and systems herein may reduce brain injury by reducing the positive pressure required from external respiratory support and counteracting the effects of aberrant vagal signaling. Multiple means may be used to reduce the positive pressure, including iron lung, extracorporeal membrane oxygenation (ECMO), as well as phrenic nerve and respiratory muscle (e.g. diaphragm, intercostal, etc.) stimulation. Aberrant vagal signaling may be mitigated by any method used to reduce pulmonary stretch receptor activation as well as with vagus/phrenic stimulation or nerve block.

FIG. 1 illustrates the anatomy of the neck and chest and, in particular, the relative locations of the left and right phrenic nerves (PhN), vagus nerves (VN), internal jugular veins (IN), brachiocephalic veins (BCV), subclavian veins (SCV) and superior vena cava (SVC). The PhNs run approximately perpendicular to and close to the BCVs in areas 107R and 107L near the IN/BCV junctions. Each PhN may have more than one branch. The branches may join together at variable locations ranging from the neck region to the chest region below the IN/BCV junctions. In the latter case, branches of the PhN on either side of the body may course on opposite sides of the BCVs. The right PhN may include branches that course on either side of the SVC. The left and right PhNs extend respectively to left and right hemi-diaphragms (HD). Upon leaving the medulla oblongata, the VN extends down the neck between the trachea and esophagus, into the chest, abdomen and further, creating an extensive information network with various organs (e.g. lungs, diaphragm, etc.), and other tissues. The right vagus nerve gives rise to the recurrent laryngeal nerve, which descends into the neck between the trachea and esophagus.

Figure 2:
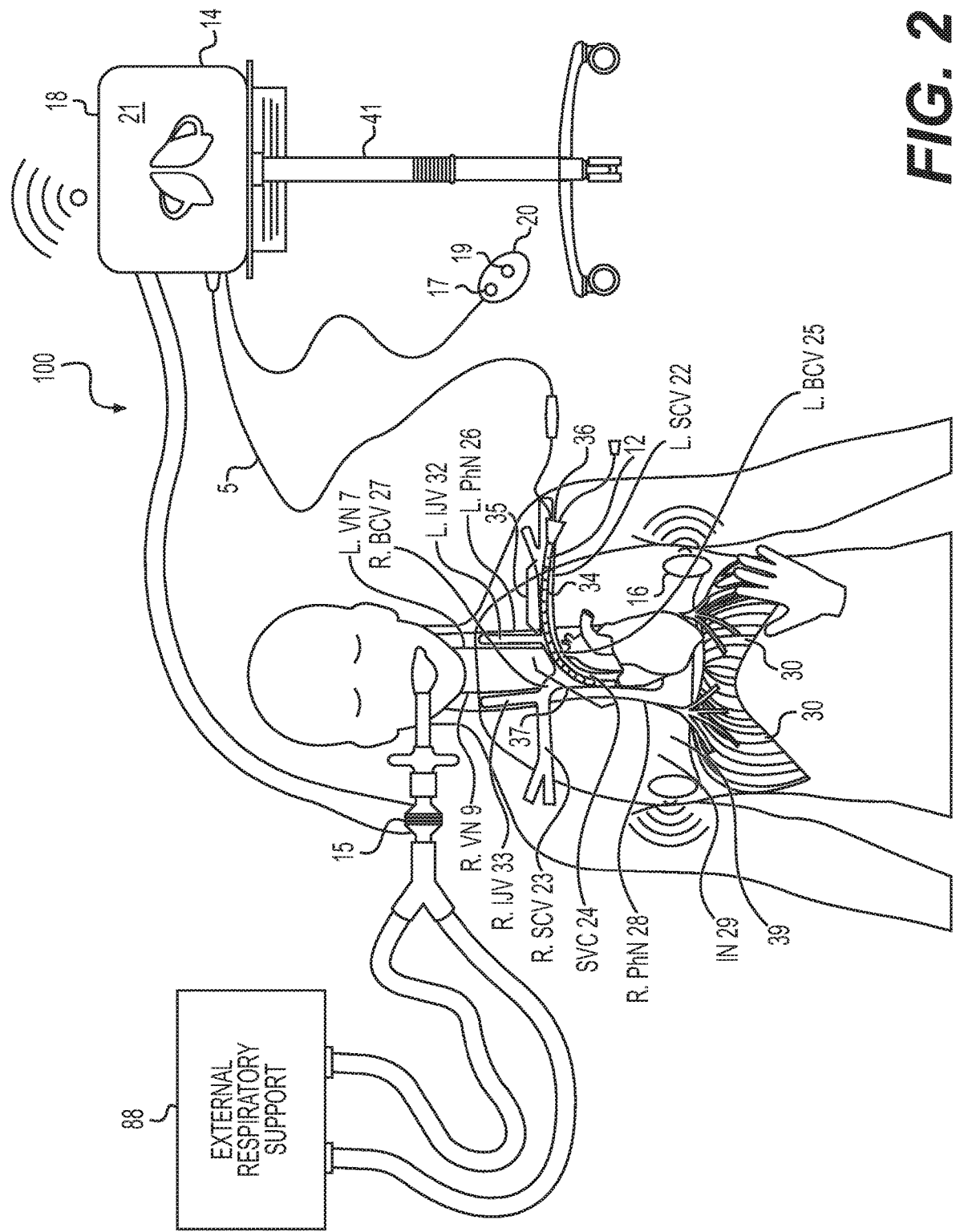
FIG. 2 illustrates the anatomy of selected nerves and blood vessels in a person's neck and upper torso, the diaphragm and intercostal respiratory muscles, an exemplary stimulation device (e.g. catheter) placed in one vein, a control unit, a sensor (e.g., motion sensor, airflow sensor, and/or pressure sensor), an exemplary remote control device, a graphical user interface, a pulse generator, and an external respiratory support device, according to an exemplary embodiment.

Referring to FIG. 2, the systems described herein may include several components, including: a stimulator having one or more electrodes or electrode assemblies, such as a transvascular nerve stimulation catheter 12 including stimulation electrodes (e.g., shown FIG. 2) or transcutaneous stimulation array 13 (FIG. 8); a signal generator 14 to provide stimulation energy to the electrode assemblies; one or more sensors 16, or means for sensing, to sense a condition of the patient and inform adjustments to the stimulation signals and/or external respiratory support; and a control unit 18 to manage the parameters associated with the delivery of the stimulation signals to the electrodes. In some embodiments, the system may incorporate a remote controller 20, a graphical user interface (GUI) 21, a touchscreen (e.g., as part of GUI 21), a hand-held controller (e.g., remote controller 20), a keyboard, a computer (e.g., control unit 18), a smart phone, a tablet, or another input device.

In some examples, the stimulator devices (e.g., catheter 12) are readily applied to, or inserted into, the patient, temporary, and easily removed from the patient without the need for surgery at a later time. The stimulator, such as catheter 12 or other stimulation array, may be positioned internal to the patient via a percutaneous incision in the patient's neck. In some cases, the stimulator may be inserted proximate subclavian, femoral, or radial regions of the patient. In other examples, as described herein, the stimulator may be positioned external to the patient.

The various system components described herein may be combined and used together in any logical arrangement. Furthermore, individual features or elements of any described example may be combined with or used in connection with the individual features or elements of other embodiments. The various examples may further be used in different contexts than those specifically described herein. For example, the disclosed electrode structures may be combined or used in combination with various deployment systems known in the art for various diagnostic and/or therapeutic applications.

FIG. 2 further illustrates the anatomy of the neck and chest and, in particular, the relative locations of the left and right phrenic nerves (L. PhN 26 and R. PhN 28), vagus nerves (L. VN 7 and R. VN 9), left and right internal jugular veins (L. IJV 32 and R. IJV 33), left and right brachiocephalic veins (L. BCV 25 and R. BCV 27), left and right subclavian veins (L. SCV 22 and R. SCV 23), the superior vena cava (SVC 24), and intercostal nerves (IN 29). FIG. 2 further illustrates a diaphragm 30 and intercostal muscles 39. The phrenic nerves 26, 28 run approximately perpendicular to and close to the subclavian veins 22, 23, or in some cases brachiocephalic veins 25, 27 near the junctions of the internal jugular veins 32, 33 and the brachiocephalic veins 25, 27. Each phrenic nerve 26, 28 may have more than one branch. The branches may join together at variable locations ranging from the neck region to the chest region below the junctions between the internal jugular veins 32, 33 and the brachiocephalic veins 25, 27. In the latter case, branches of the phrenic nerves 26, 28 on either side of the body may course on opposite sides of the brachiocephalic veins 25, 27. The right phrenic nerve 28 may include branches that course on either side of the superior vena cava 24. The left and right phrenic nerves 26, 28 extend respectively to left and right hem i-diaphragms.

FIG. 2 also illustrates a medical system 100 that includes transvascular nerve stimulation catheter 12 and control unit 18. Catheter 12 may include a plurality of electrodes 34. Catheter 12 may be operably connected (e.g., hardwired via cable 5, wireless, etc.) to control unit 18. Control unit 18 may be programmed to perform any of the functions described herein in connection with system 100. In some embodiments, control unit 18 may include a remote controller 20 to allow a patient or health professional to control operation of control unit 18 at a distance from the control unit 18. The remote controller 20 may include a handheld device, as illustrated in FIG. 2. In some examples, remote controller 20 may include a hand switch, foot switch/pedal, a voice-activated, touch-activated, or pressure-activated switch, a remote switch, or any other form of a remote actuator. The control unit 18 may include a touch screen and may be supported by a cart 41.

The remote controller 20 may include buttons 17, 19 that can be pressed by a patient or other user to control breathing patterns. In one example, pressing one of buttons 17, 19 can initiate a "sigh" breath, which may cause a greater volume of air to enter the patient's lungs than in a previous breath. A sigh breath may result when electrodes 34 of catheter 12 are directed to stimulate one or more of the phrenic nerves 26, 28 at a higher level than a normal breath (e.g., a stimulation train having a longer duration of stimulation or having pulses with a higher amplitude, pulse width, or frequency). Higher amplitude stimulation pulses can recruit additional nerve fibers, which in turn can engage additional muscle fibers to cause stronger and/or deeper muscle contractions. Extended pulse widths or extended durations of the stimulation train can deliver stimulation over longer periods of time to extend the duration of the muscle contractions. In the case of diaphragm muscle stimulation, longer pulse widths or extended duration of stimulation (train of pulses) have the potential to help expand the lower lung lobes by providing greater or extended negative pressure around the outside of the lungs. Such negative pressure has the potential to help prevent or mitigate a form of low pressure lung injury known as atelectasis. The increase in stimulation frequency can result in a more forceful contraction of the diaphragm 30. The increased stimulation (e.g., higher amplitude, pulse width, stimulation duration, or frequency) of the one or more phrenic nerves 26, 28 may result in a more forceful contraction of the diaphragm 30, causing the patient to inhale a greater volume of air, thereby providing a greater amount of oxygen to the patient. Sigh breaths may increase patient comfort.

In other examples, buttons 17, 19 may allow the patient or other user to start and stop stimulation therapy, or to increase or decrease stimulation parameters, including stimulation charge (amplitude×pulse width), frequency of pulses in a stimulation train, or breath rate. LED indicators or a small LCD screen (not shown) on the remote controller 20 or control unit 18 may provide other information to guide or inform the operator regarding the stimulation parameters, the feedback from the system sensors, or the condition of the patient.

Figure 7:
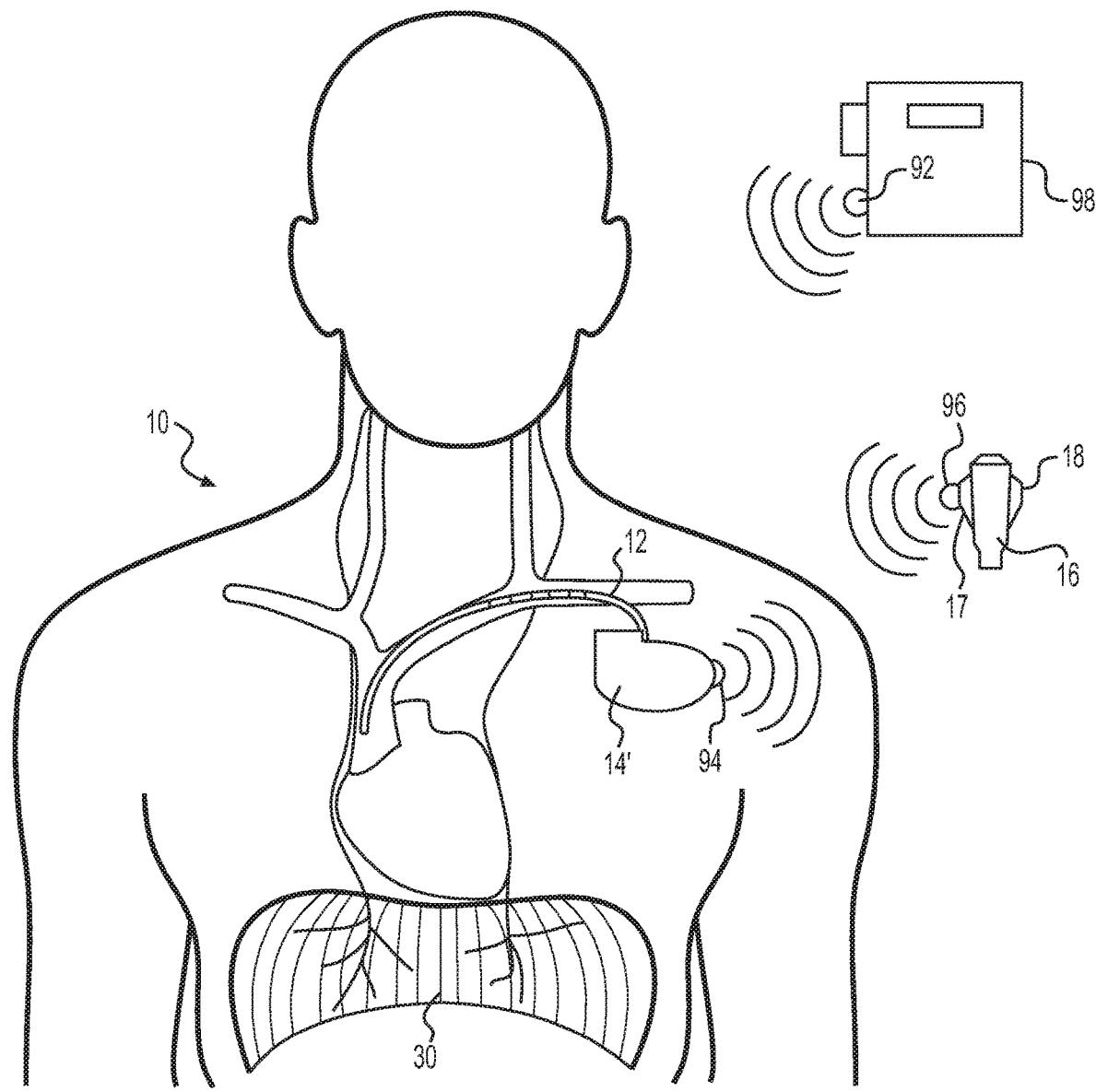
FIG. 7 illustrates the anatomy of selected nerves and blood vessels in a person's neck and upper torso along with an exemplary implanted stimulation device (e.g. catheter and pulse generator), a control button, and a control unit connected via a wireless connection, according to an exemplary embodiment.

Alternatively, a control unit having the functionality of control unit 18 can be implanted in the patient, along with catheter 12 as illustrated in FIG. 7. In this example, a remote controller and a programmer may communicate with the implanted control unit wirelessly. Each of the programmer, the implanted control unit, and remote controller may include a wireless transceiver so that each of the three components can communicate wirelessly with each other. The implanted control unit may include all of the electronics, software, and functioning logic necessary to perform the functions described herein. Implanting the control unit may allow catheter 12 to function as a permanent breathing pacemaker. A programmer may allow the patient or health professional to modify or otherwise program the nerve stimulation or sensing parameters. In some examples, remote controller 20 may be used as described in connection with FIGS. 2, 3 and 8. In other examples, remote controller 20 may be in the form of a smartphone, tablet, watch, or other suitable input device.

In yet another additional or alternative example, the control unit of system 100 may be portable. The portable control unit may include all of the functionality of control unit 18 of FIG. 2, but it may be carried by a patient or other user to provide the patient with more mobility and may be disconnected from the cart 41. In addition to carrying the portable control unit, the patient can wear the control unit on a belt, on other articles of clothing, or around his/her neck, for example. In other examples, the portable control unit may be mounted to a patient's bed to minimize the footprint of system 100 in the area around the patient, or to provide portable muscle stimulation in the event a bed-ridden patient needs to be transported or moved to another location.

The distal tip of catheter 12 may be a tapered distal end portion of catheter 12 and may have a smaller circumference than the body of catheter 12. The distal tip may be open at the distal end to allow a guide wire to pass through and distally beyond catheter 12. The distal tip may be softer than other portions of catheter 12, be atraumatic, and have rounded edges. Catheter 12 also may have one or more ports or openings in the sidewall of the catheter. A first opening may be located at a mid-portion of catheter 12 and other openings may be located near a proximal end of catheter 12. Each opening may be in fluid communication with respective lumens in catheter 12, through which fluid can be infused or extracted. The fluid may exit and/or enter the ports to be delivered into and/or from a blood vessel.

During use, a proximal portion of catheter 12 may be positioned in left subclavian vein 22, and a distal portion of catheter 12 may be positioned in superior vena cava 24. Positioned in this manner, electrodes 34 on the proximal portion of catheter 12 may be positioned proximate left phrenic nerve 26, and electrodes 34 on the distal portion of catheter 12 may be positioned proximate right phrenic nerve 28. As an alternative insertion site, catheter 12 may be inserted into a jugular vein e.g., left jugular vein 32 such as left external jugular vein or left internal jugular vein or right jugular vein 33 such as right external jugular vein or right internal jugular vein, and superior vena cava 24, such that the proximal electrodes are positioned to stimulate left phrenic nerve 26 and the distal electrodes are positioned to stimulate right phrenic nerve 28.

Left and right phrenic nerves 26, 28 may innervate diaphragm 30. Accordingly, catheter 12 may be positioned to electrically stimulate one or both of the left and right phrenic nerves 26, 28 to cause contraction of the diaphragm muscle 30 (or a portion thereof) to initiate or support a patient breath, help reduce the pressure from the mechanical ventilator, open up the lower lungs, reduce lung stretch/injury, and/or reduce aberrant brain signaling which may lead to cognitive injury.

In further examples, catheter 12 can be placed into and advanced through other vessels providing access to the locations adjacent the target nerve(s) (e.g., phrenic nerves), such as: the jugular, axillary, cephalic, cardiophrenic, brachial, or radial veins. In addition, the stimulator (e.g., catheter 12 or array 13) may use other forms of stimulation energy, such as ultrasound, to activate the target nerves. In some examples, the system 100 can target other respiratory muscles (e.g., intercostal) either in addition to, or alternatively to, the diaphragm 30. The energy can be delivered via one or more types of electrodes/methods including transvascular electrodes, subcutaneous electrodes, electrodes configured to be positioned in contact with the nerve (e.g., nerve cuffs), transdermal electrodes/stimulation, or other techniques known in the field.

The nerve stimulation systems and methods described herein may reduce or eliminate the need for a patient to receive external respiratory support. External respiratory support 88 in FIG. 2 can include any devices or methods to help correct or otherwise enhance blood gases and/or reduce the work of breathing of a patient. Some non-limiting examples include mechanical ventilation, non-invasive ventilation (NIV), CPAP, BiPAP, nasal cannula oxygenation, DPS (Synapse, Avery, etc.), and ECMO, as described below.

Mechanical ventilation may refer to use of a ventilator to assist or replace spontaneous breathing. Mechanical ventilation is termed "invasive" if it involves any instrument penetrating through the mouth (such as an endotracheal tube) or the skin (such as a tracheostomy tube). There are two main types of mechanical ventilation: positive pressure ventilation, where air (or another gas mix) is forced into the trachea via positive pressure, and negative pressure ventilation, where air is drawn into (e.g., sucked into) the lungs (e.g., iron lung, etc.). There are many modes of mechanical ventilation. Mechanical ventilation may be indicated when the patient's spontaneous ventilation is unable to provide effective gas exchange in the lungs.

Ventilation also can be provided via a laryngeal mask airway (e.g., laryngeal mask), which is designed to keep a patient's airway open during anesthesia or unconsciousness. It is often referred to as a type of supraglottic airway. A laryngeal mask may include an airway tube that connects to an elliptical mask with a cuff, which is inserted through the patient's mouth and down the windpipe. Once deployed, the device may form an airtight seal on top of the glottis (unlike tracheal tubes, which pass through the glottis) to provide a secure or stable airway.

Non-invasive ventilation (NIV) is the use of airway support administered through a face (e.g., oral, nasal, nasal-oral) mask/cannula instead of an endotracheal tube. Inhaled gases are given with positive end-expiratory pressure, often with pressure support or with assist control ventilation at a set tidal volume and rate. This type of treatment is termed "non-invasive" because it is delivered with a mask or other means that is fitted to the face or nose, but without a need for tracheal intubation. Other forms of non-invasive ventilation include the use of external negative pressure systems such as is used in an iron-lung. Any device used to reduce the pressure outside the chest cavity or torso of a patient could effectively provide NIV.

Continuous positive airway pressure (CPAP) is a form of positive airway pressure ventilation, which applies mild air pressure on a continuous basis to keep the airways continuously open. CPAP may be used for patients who are able to breathe spontaneously on their own but may require a level of pressure support. It is an alternative to positive end-expiratory pressure (PEEP). Both modalities stent the lungs' alveoli open and therefore help recruit more of the lungs' surface area for ventilation. PEEP generally refers to devices that impose positive pressure only at the end of an exhalation. CPAP devices apply continuous positive airway pressure throughout the breathing cycle. Thus, the ventilator itself does not cycle during CPAP, no additional pressure above the level of CPAP is provided, and patients must initiate each breath on their own.

Bilevel Positive Airway Pressure (BiPAP) therapy is very similar in function and design to CPAP. BiPAPs can also be set to include a breath timing feature that measures the amount of breaths per minute a person should be taking. If the time between breaths exceeds the set limit, the machine can force the person to breath by temporarily increasing the air pressure. The main difference between BiPAP and CPAP machines is that BiPAP machines generally have two pressure settings: the prescribed pressure for inhalation (ipap), and a lower pressure for exhalation (epap). The dual settings allow the patient to move more air in and out of their lungs.

Extracorporeal membrane oxygenation (ECMO), which is also known as extracorporeal life support (ECLS), is an extracorporeal technique to provide prolonged cardiac and respiratory support to patients whose heart and lungs are unable to provide an adequate amount of gas exchange. The technology for ECMO is similar to that used during cardiopulmonary bypass, which is typically used to provide shorter-term support. During ECMO, blood is removed from the person's body and passed through a device, which removes carbon dioxide and provides oxygen to red blood cells. Long-term ECMO patients can often develop respiratory muscle weakness because of muscle inactivity and other causes. Certain therapy methods described herein may include delivering stimulation therapy to a patient receiving both ECMO and another form of external respiratory support. Certain therapy methods of this disclosure may utilize ECMO devices, which include a stimulation array, to deliver the described therapy.

In some examples, catheter 12 can be inserted into (and/or secured relative to) the patient. In many embodiments, catheter 12 may be removed from the patient's body when desired without the need for surgery. For example, catheter 12 of FIG. 3 may be withdrawn once the patient is breathing independently.

The timing of stimulation of one or more nerves may be coordinated with the timing of ventilation. For example, a nerve (e.g., a vagus nerve) may be stimulated during at least a portion of a ventilation inspiration period.

Alternatively or additionally, timing of stimulation of multiple nerves may also be coordinated. For example, stimulation of a second nerve is performed while a first nerve is not stimulated by the one or more electrodes of a first plurality of the electrodes of the catheter. In some cases, stimulating one or more portions of a respiratory muscle (e.g., diaphragm muscle) may be stimulated when a nerve is not stimulated (e.g., when the nerve is blocked, or no stimulation is provided). In some cases, stimulation output from one or more nerve stimulation electrodes may occur in an inverse relationship to stimulation output from the two or more diaphragm stimulation electrodes. Alternatively or additionally, stimulation output from the one or more nerve stimulation electrodes may occur during stimulation output from the two or more diaphragm stimulation electrodes.

Figure 3:
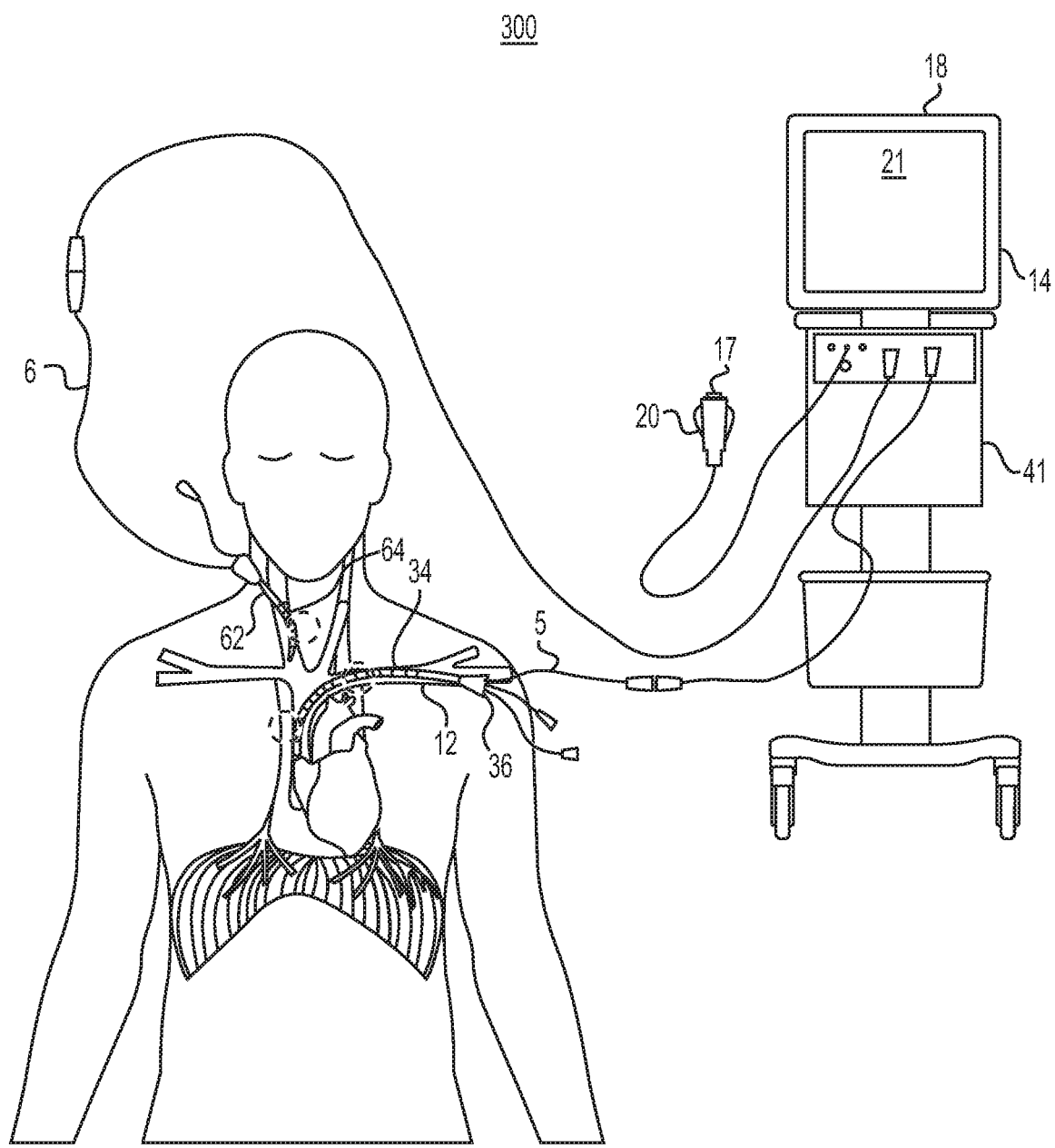
FIG. 3 illustrates the anatomy of selected nerves and blood vessels in a person's neck and upper torso, along with a first exemplary stimulation device (e.g. catheter) placed in a first location (e.g. vein, artery, skin, etc.) and a second exemplary stimulation device (e.g. catheter) placed in a second location (e.g. vein, artery, skin, etc.), in addition to a control unit.

FIG. 3 illustrates an exemplary medical system 300 that includes two catheters (12 and 62), each catheter including one or more lumens and having electrodes assemblies (34 and 64) that include proximal electrode assemblies and distal electrode assemblies. The proximal electrode assemblies and the distal electrode assemblies of each catheter may each include at least one electrode set or a plurality of electrode sets. The electrode assemblies 34 and 64 may be positioned on or within a tubular member or catheter body of catheter 12 or 62. Catheters 12 and 62 may be positioned within a patient through the patient's external or internal jugular veins, brachiocephalic veins, superior vena cava, brachial vein (not shown), radial vein (not shown), and/or left subclavian vein. The catheters 12 and 62 may be positioned such that at least one of the electrode sets is directed towards a phrenic nerve, and at least one of the electrode sets is directed towards a vagus nerve. For example, the catheters 12 and 62 may be positioned such that at least one of the electrode sets is directed towards the left phrenic nerve, at least one of the electrode sets is directed laterally towards the right phrenic nerve, and at least one of the electrode sets is directed towards a vagus nerve. As such, when positioned, catheters may receive signals from a control unit 14 and, using electrodes or the electrode sets, stimulate the left phrenic nerve and/or the right phrenic nerve and/or one or both of the vagus nerves. As shown in FIG. 3, catheter 12 may be configured to stimulate the left and the right vagus nerves, and catheter 62 may be configured to stimulate the right vagus nerve and the right phrenic nerve. Catheters may further include a manifold 36 that extends external to the patient. Electrical cables and pigtail lumens may extend from manifold 36. At least one electrical cable 5 or 6 and pigtail lumen may include cable connectors to connect to external elements, and electrical cables may be coupled to electrical control unit 14 via a cable connector. The electrical cables may be formed of electrical leads that connect to electrode assemblies. Cable connectors may be attached (e.g. by solder, crimp, PCB, etc.) to the cables, and one or both of the cable connectors may include a threading. Alternatively or additionally, one or both of cable connectors may include a push-to-pull compression fitting or a slip-lock fitting (not shown). Control unit 14 and other elements may be electronically connected to the components within catheter 12, 62 to both send and receive signals and/or data to selectively stimulate electrode sets and/or monitor the patient and any response to the stimulation. Alternatively or additionally, the cables may include one or more lumens or fluid lines that connect to one or more internal lumens in catheter 12, 62. Additionally the system may contain a push button 17 to trigger the stimulation or sensing or any other function of the control unit 14.

Figure 4A:
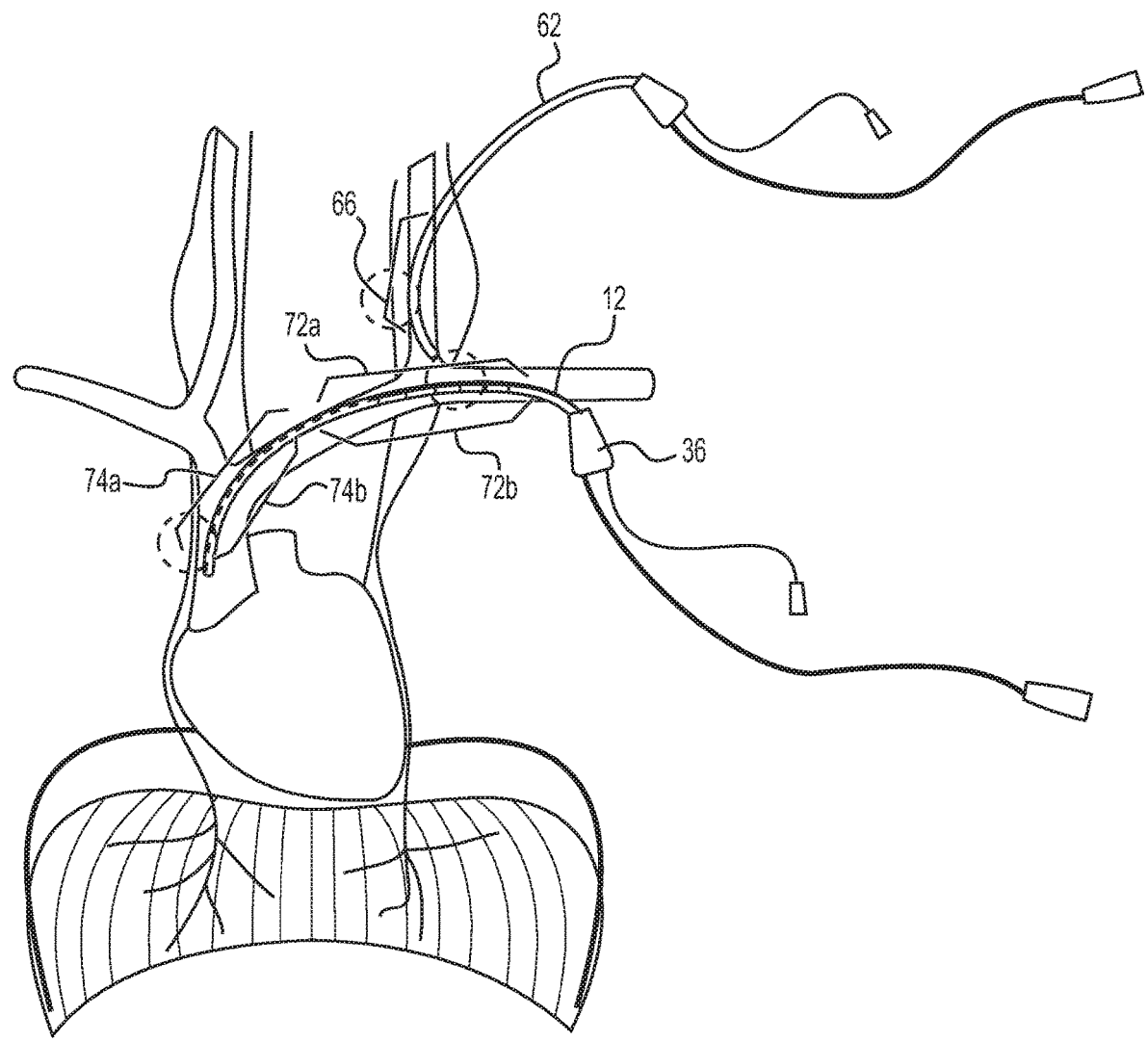
FIG. 4A illustrates a ventral view of a pair of exemplary catheters having windows that may align with nerve-stimulating electrodes within the catheter, with the exemplary catheters inserted in a person's neck and upper torso, according to an exemplary embodiment.

As shown in FIG. 4A, a subclavian catheter 12 may include two axially extending populations of proximal apertures or windows (72a and 72b). Each axially extending population includes windows. The electrodes and corresponding windows may be of any shape (e.g. circular, oval, crescent, oblong, rectuangular, etc.). In one embodiment, a majority of the windows within each population are positioned within the same 180 degree circumferential position around the exterior of catheter, whereby the 180 degree circumferential position may differ between the first and second electrode populations (e.g. have different axial positions along the exterior of catheter). In another embodiment the two populations of windows 72a and 72b may be substantially longitudinally aligned (e.g. within the same 90 degree circumferential position) and the 90 degree circumferential position of the first population and the second population are different, although potentially overlapping. For instance, as illustrated in FIG. 4A, one proximal window of a first row 72a is located at the same axial position as a window of a second row 72b, but at a different circumferential position around the exterior of the catheter. When positioned in a patient, the two rows of proximal windows 72a and 72b may be substantially posterior facing, and at least one proximal window may face, abut or be positioned in the vicinity of the left phrenic nerve. The catheter may also include two axially extending rows of distal apertures or windows (74a and 74b). Again, each axially extending row (74a, 74b) includes distal windows positioned at the same circumferential position around the exterior of catheter, but at different axial positions along the exterior of catheter. The two rows of distal windows 74a and 74b may be unaligned such that one distal window of a first row is axially between two distal windows of a second row. For instance, as illustrated in FIG. 4A, one distal window of a first row 74a is located at a different axial position and at a different circumferential position around the exterior of the catheter than a window of the second row 74b. When positioned in a patient, the two rows of distal windows 74a and 74b may be substantially laterally facing (to the patient's right), and at least one distal window may face, abut, or be positioned in the vicinity of the right phrenic nerve. In the example shown in FIG. 4A, when viewed ventrally, two unaligned rows (74a, 74b) of three distal windows may appear as one row of six distal windows, because one row is anterior facing and one row is posterior facing.

As shown in FIG. 4A, a separate jugular catheter 62 may be inserted in either left jugular veins or right jugular veins. The jugular catheter may include a population of apertures or windows 66 such that when positioned in a patient, at least one window may face, abut, or be positioned in the vicinity of the vagus nerve.

Windows on catheters may expose electrodes, allowing for a conductive path between sets or pairs of electrodes and surrounding tissue, including the blood vessel lumen in which catheter is inserted. Alternatively, electrodes could be printed onto the surface of the catheter by one of several known means (e.g. conductive inks, polymers, etc.). Further, the electrodes may be integrated into a flexible printed circuit, which can be attached to, or integrated into, the catheter. Insulation means known in the art would be used to ensure that the electrodes, and not any unwanted electrical elements, are exposed to direct contact with the patient.

Figure 4B:
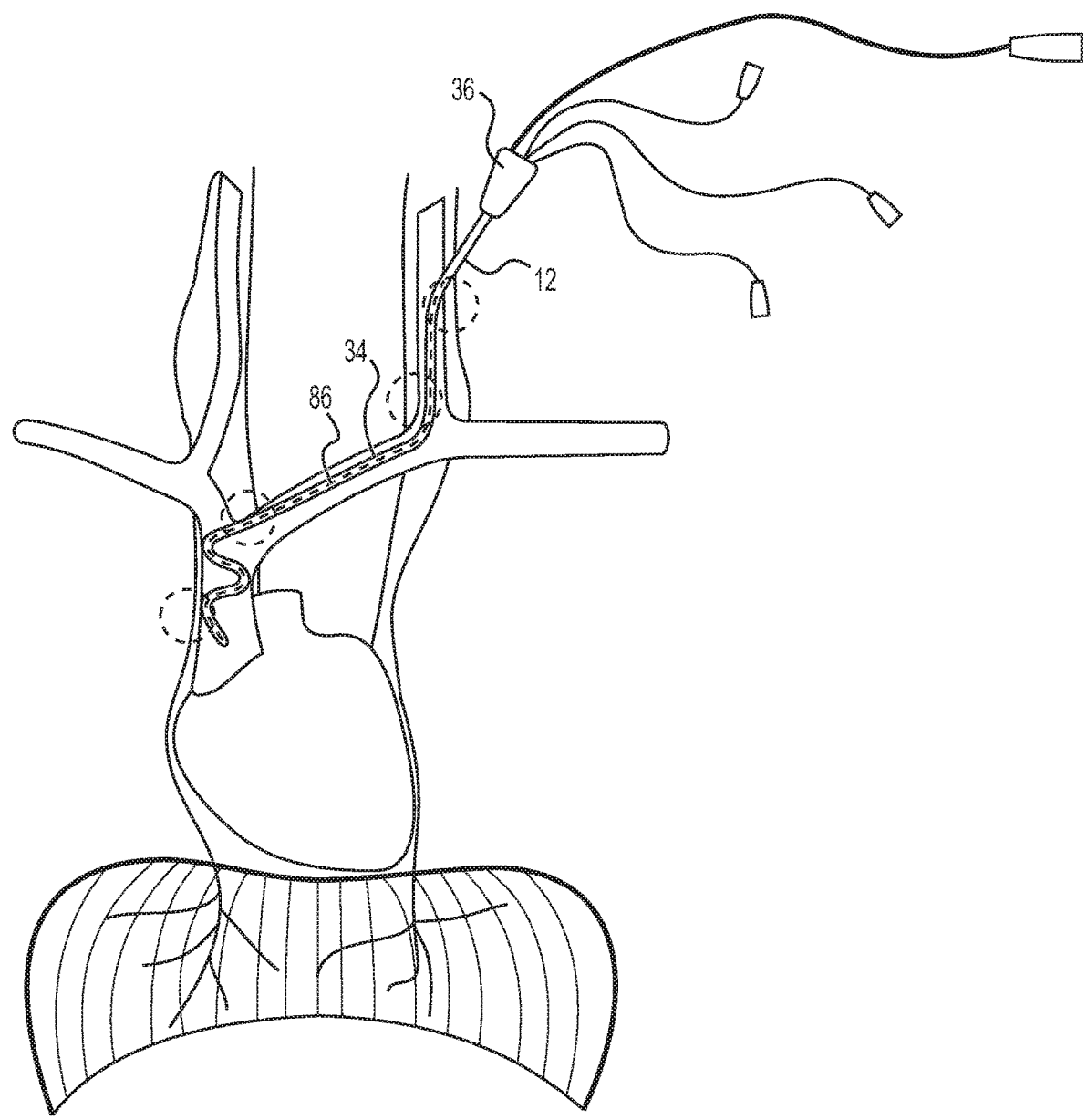
FIG. 4B illustrates a ventral view of a single exemplary catheter with location securement means (e.g. anchor, adhesive, expandable coil/helix, etc.), the catheter having windows that may align with nerve-stimulating electrodes within the catheter, with the exemplary catheter inserted in a person's neck and upper torso, according to an exemplary embodiment.

FIG. 4B shows a single catheter 12 placed through a jugular vein into the superior vena cava. The catheter 12 may include rows of apertures or windows 86 positioned proximally, medially and distally, such that when catheter 12 is positioned in a patient, at least one window may face, abut, or be positioned in the vicinity of the left phrenic nerve, at least one window may face, abut, or be positioned in the vicinity of the right phrenic nerve, and/or at least one window may face, abut, or be positioned in the vicinity of a vagus nerve. Windows 86 on catheters may expose electrodes, allowing for a conductive path between sets or pairs of electrodes and surrounding tissue, including the blood vessel lumen in which catheter is inserted. The catheter 12 may include a feature to secure or stabilize the catheter within the patient, and or the electrodes at a specific location. In one embodiment catheter 12 may have a helical shape at the distal end or proximal end or both. This shape can be formed by heat setting the polymer sheath or tube, or by adding a shaped stainless steel wire or a shape memory nitinol wire or any other shape memory alloy. A shape-memory alloy may activate the helical shape when heated to a temperate between 30° C. to 45° C., e.g., 37° C. This helical shape may help in adding vessel wall apposition and, in turn, may aid in fixing the catheter in the current location. The helical shape may also increase coverage of electrodes in the radial orientation of the blood vessels. This single catheter can be used to stimulate the phrenic nerves (PNs) and or vagus nerves (VNs).

In one example illustrated in FIG. 4B, the distal or proximal portion of catheter 12 may be configured to assume a helical shape when positioned within the patient to help anchor catheter 12 to the vessel wall or to stabilize catheter 12 during nerve stimulation. The helical shape may position electrodes 34 at different radial positions within the vessel and relative to target nerves. Selecting electrodes 34 at different radial positions within the vessel (whether or not due to any helical shape), or at different distances from the target neve (whether or not due to any helical shape), may be useful for nerve stimulation. For example, in certain instances it may be desirable to stimulate the nerve with electrodes 34 that are closer to the nerve (e.g., to obtain a stronger respiratory muscle response), and in other instances it may be desirable to stimulate the nerve with electrodes 34 that are farther away from the nerve (e.g., to obtain a weaker respiratory muscle response, or prevent stimulation of unwanted nerves).

Figure 5:
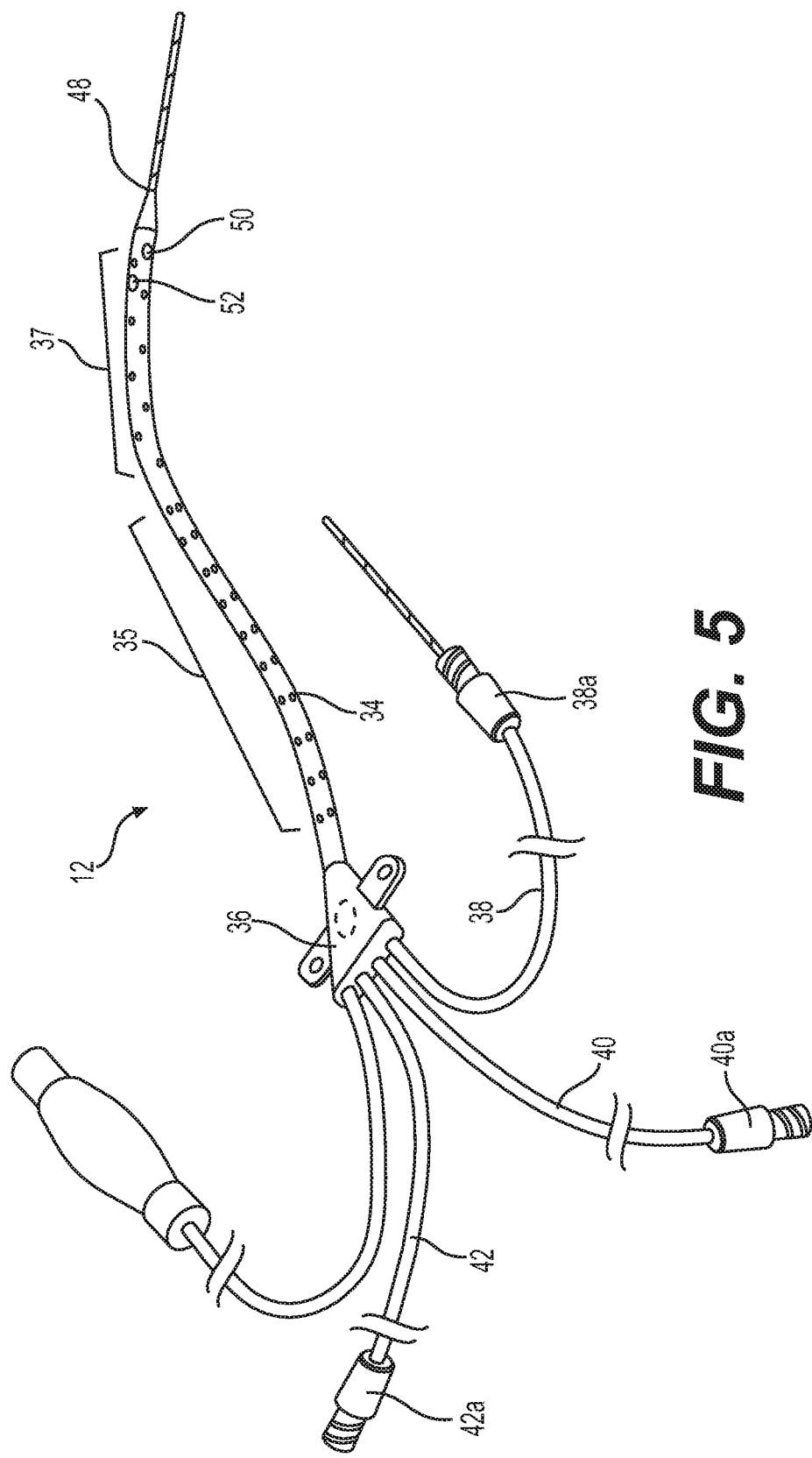
FIG. 5 illustrates a perspective view of an exemplary catheter with conductors and electrodes exposed on an exterior of the catheter and including fluid transport lumens, according to an exemplary embodiment.

Referring to FIG. 5, catheter 12 may include a stimulation array comprising a plurality of electrodes 34 or other energy delivery elements. In one example, electrodes 34 may be surface electrodes located on an outer wall of catheter 12. In another example, electrodes 34 may be positioned radially inward relative to the outer wall of catheter 12 (e.g., exposed through openings or windows in the outer wall). In yet another example, the electrodes 34 may include printed electrodes as described in U.S. Pat. No. 9,242,088, which is incorporated by reference herein.

Electrodes 34 may extend partially around the circumference of catheter 12. This "partial" electrode configuration may allow electrodes 34 to target a desired nerve for stimulation, while minimizing application of electrical charge to undesired areas of the patient's anatomy (e.g., other nerves or the heart). As shown in FIG. 5, catheter 12 may include a proximal set 35 of electrodes 34 configured to be positioned proximate to and stimulate left phrenic nerve 26 and a distal set 37 of electrodes 34 configured to be positioned proximate to and stimulate right phrenic nerve 28. Electrodes 34 may be arranged in populations extending along the length of catheter 12. In one example, proximal set 35 may include two rows of electrodes 34 extending parallel to a longitudinal axis of catheter 12, and distal set 37 may include two rows of electrodes 34 extending parallel to a longitudinal axis of catheter 12.

Furthermore, the catheters described herein may include any features of the nerve stimulation devices and sensing devices described in the following documents, which are all incorporated by reference herein in their entireties: U.S. Pat. No. 8,571,662 (titled "Transvascular Nerve Stimulation Apparatus and Methods," issued Oct. 29, 2013); U.S. Pat. No. 9,242,088 (titled "Apparatus and Methods for Assisted Breathing by Transvascular Nerve Stimulation," issued Jan. 26, 2016); U.S. Pat. No. 9,333,363 (titled "Systems and Related Methods for Optimization of Multi-Electrode Nerve Pacing," issued May 10, 2016); U.S. application Ser. No. 14/383,285 (titled "Transvascular Nerve Stimulation Apparatus and Methods," filed Sep. 5, 2014); U.S. application Ser. No. 14/410,022 (titled "Transvascular Diaphragm Pacing Systems and Methods of Use," filed Dec. 19, 2014); U.S. application Ser. No. 15/606,867 (titled "Apparatus And Methods For Assisted Breathing By Transvascular Nerve Stimulation," filed May 26, 2017); or U.S. application Ser. No. 15/666,989 (titled "Systems And Methods For Intravascular Catheter Positioning and/or Nerve Stimulation," filed Aug. 2, 2017). In addition, the control units described herein can have any of the functionality of the control units described in the above-referenced patent documents (e.g., the control units described herein can implement the methods of nerve stimulation described in the incorporated documents).

During nerve stimulation, one or more electrodes 34 may be selected from the proximal set 35 for stimulation of the left phrenic nerve 26, and one or more electrodes 34 may be selected from the distal set 37 for stimulation of right phrenic nerve 28. Catheter 12 may stimulate nerves using monopolar, bipolar, or tripolar electrode combinations, or using any other suitable combination of electrodes 34. In some examples, a second or third group of electrodes can be used to stimulate other respiratory muscles. In general, a stimulator or a stimulation array may include multiple sets of electrodes, with each set being configured to stimulate either the same or different nerves or muscles. When multiple nerves or muscles are being stimulated, the controllers and sensors described herein may be used to coordinate stimulation to achieve the desired muscle activation, breath, or level of respiratory support.

As illustrated in FIG. 5, catheter 12 may further include one or more lumens. Each lumen may extend from a proximal end of catheter 12 to a distal end of catheter 12, or to a location proximate the distal end of catheter 12. In some examples, lumens may contain or be fluidly connected to sensors, such as blood gas sensors, electrical sensors, motion sensors, flow sensors, or pressure sensors. In some examples, catheter 12 may include three lumens (not shown) that may connect with extension lumens 38, 40, 42 that extend proximally from hub 36. Any lumens within catheter 12 may terminate in one or more distal ports 52, 50, 48 either at the distal end of catheter 12 or in a sidewall of catheter 12. In one example, the lumens may be used to transport fluid to and from the patient, such as to deliver medications or withdraw blood or other bodily fluids, remove $CO_2$, infuse oxygen, etc. In other examples, these lumens may be used to hold a guidewire, stiffening wire, optical fiber camera, sensors, or other medical devices. For example, FIG. 5 illustrates an optical fiber camera 46 inserted into lumen 38, extending through a corresponding internal lumen, and exiting from distal port 48. The electrodes 34 may be configured to sense physiological information from a patient, such as properties of blood, nerve activities, ECG, or electrical impedance.

Catheter 12, or other stimulation devices of this disclosure, may incorporate markings or other indicators on its exterior to help guide the positioning and orientation of the device. Catheter 12, or other stimulation devices of this disclosure, may also include internal indicators (e.g., radiopaque markers, contrast material such as barium sulfate, echogenic markers, etc.) visible by x-ray, ultrasound or other imaging technique to assist with positioning the stimulator in the desired location. Catheter 12 may include any combination of the features described herein. Accordingly, the features of catheter 12 are not limited to the specific combination shown in FIG. 5.

Referring still to FIG. 5, a hub 36 may be connected to the proximal end of catheter 12. Hub 36 may include a conductive surface and can act as a reference electrode during monopolar stimulation or sensing. In some embodiments, hub 36 may be sutured on a patient's skin. In addition, hub 36 may be used as an ECG or other reference electrode.

The embodiment illustrated in FIG. 5 incudes a catheter 12 having twenty proximal windows 35 (two rows of ten windows) and eight distal windows 37 (two rows of four windows). However, in other embodiments, the catheter may include fewer or more rows and various numbers of proximal or distal windows. For example, in other embodiments, the catheter may include two, four, eight, ten, twelve, or more proximal windows arranged in one, two, three, or more rows, and/or two, four, six, ten, twelve or more distal windows arranged in one, two, three, or more rows. The number of windows may also be an odd number. The windows may be cut (e.g. by a laser, manual skive, drill, punch, etc.) through the exterior wall of catheter 12, or the windows may be formed by any other suitable method, such as during an extrusion process, 3-D printing, or other manufacturing process. The windows may have a rectangular, oval, square, or any other shape. The windows may be apertures configured to allow electrical signals to travel from an interior lumen of the catheter to the exterior of the catheter. Each window may contain an electrode that is exposed through the window and connected electrically, independently of other electrodes to the control unit. U.S. patent application Ser. No. 15/606,867, which is incorporated by reference, discusses such connections. In an additional or alternative embodiment, the windows may be covered by a material that allows electrical signals to pass through.

The dimensions of catheter 12 may be customized in accordance with the anatomy of a particular patient (e.g., different sizes of humans, pigs, chimpanzees, etc.). However, in some embodiments, the length of the section of the catheter that includes the proximal windows may be 16 cm or less, between 3 and 5 cm, or between 1 and 3 cm. The length of the section of the catheter that includes the distal windows may be 12 cm or less, between 2 and 4 cm, or between 1 and 2 cm. The distance between two adjacent windows (whether the windows are circumferentially adjacent or longitudinally adjacent on the same row of windows) may be 5 cm or less, 3 cm or less, may be around 1 cm, or may be less than 1 cm. These catheter dimensions are exemplary only, and the catheter may have dimensions that vary from the above ranges and specific measurements. Additionally, catheter 12 may include windows in different configurations than discussed above.

The catheter's distal tip may be a tapered distal end portion of catheter 12. The distal tip may be open at the distal end to allow a guide wire to pass through and distally beyond catheter. The distal tip may have a smaller circumference than the body of catheter, and may be softer than other portions of catheter, atraumatic, and have rounded edges.

The catheter may also have a ports 38a, 40a, 42a that are connected to an individual tube proximally 48, 50, 52 to act as one or more separate vascular lines (three as shown in FIG. 5) to help infuse different fluids.

Figure 6:
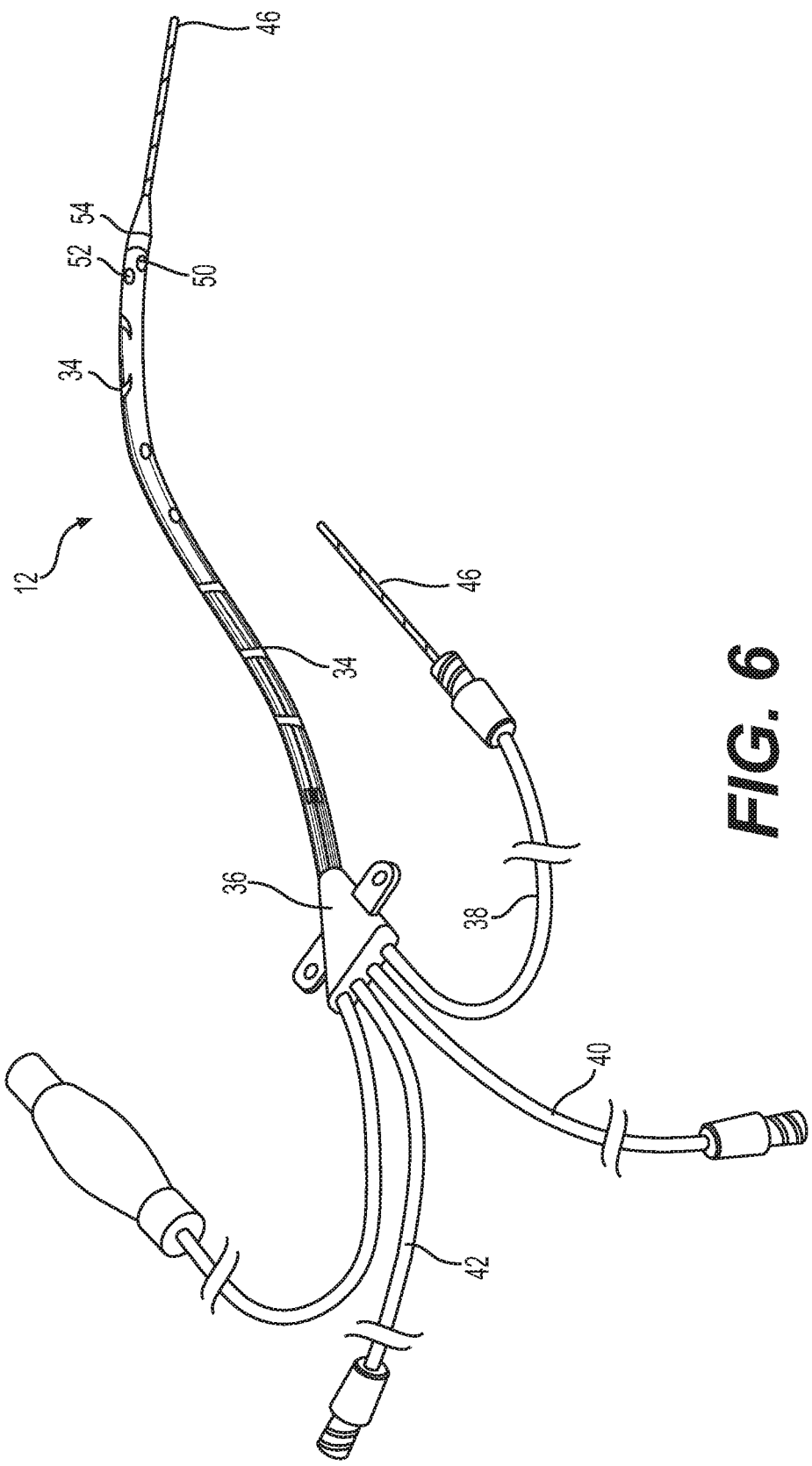
FIG. 6 illustrates an exemplary stimulation catheter with flexible electrical leads, circuits, and electrodes.

FIG. 6 illustrates another example of catheter 12. Catheter 12 shown in FIG. 6 is similar to the catheter of FIG. 5, except that electrodes 34 may be formed by conductive inks (such as silver, gold, graphene, or carbon flakes suspended in polymer or other media) printed on the surface of catheter 12, as described in U.S. Pat. No. 9,242,088, incorporated by reference herein. These conductive inks may be deposited and adhered directly onto catheter 12 and sealed, except for the exposed electrodes 34, with outer polyurethane or other flexible insulative film/material. The electrodes may be in the form of a flexible solid-state circuit that is attached or incorporated into or onto a lead, catheter, or another surface. The exposed electrodes 34 may be coated (e.g., with titanium nitride) for purposes such as one or more of: enhancing electrical properties, such as conductivity and surface area; providing corrosion resistance; and reducing the potential for formation of silver oxide, which could be toxic. As shown in FIG. 6, the conductive ink trace of distal electrodes may travel proximally along catheter 12 past the more proximal electrodes 34. FIG. 6 further illustrates catheter 12 having an ultrasound transducer 54 or other sensor at a distal end of catheter 12.

FIG. 7 illustrates an alternative medical system with similar elements to the medical system of FIG. 2. This medical system includes a wireless connection from control unit 14' to catheters 12 and a wireless connection from a push button or buttons to the control unit 14'. In this exemplary system 10, control unit 14' is implanted in the patient, along with catheter 12. System 10 may further include remote controller 16 and a programmer 98 that communicates with control unit 14' wirelessly. In this embodiment, each of programmer 98, control unit 14', and remote controller 16 may include a wireless transceiver 92, 94, 96, respectively, so that each of the three components can communicate wirelessly with each other. Control unit 14' may include all of the electronics, software, and functioning logic necessary to perform the functions described herein. Implanting control unit 14' as shown in FIG. 7 may allow catheter 12 to function as a permanent breathing pacemaker. Programmer 98 may allow the patient or health professional to modify or otherwise program the nerve stimulation or sensing parameters. Remote controller 16 may be used as described in connection with FIGS. 2 and 3. In other examples, remote controller 16 may be in the form of a smartphone, tablet, watch or other wearable device. Catheter 12 or multiple catheters may be inserted and positioned as discussed with respect to FIGS. 2, 3, 4A, and 4B.

Once the catheter is fully inserted into the patient, various electrodes or electrode combinations may be tested to locate nerves of interest and to determine which electrodes most effectively stimulate the nerves of interest. For example, in one embodiment, testing may be done to locate the right phrenic nerve and to determine which group of distal electrodes in the distal electrode assemblies most effectively stimulate the right phrenic nerve. Similarly, testing may be done to locate the left phrenic nerve and to determine which group of proximal electrodes in the proximal electrode assemblies most effectively stimulate the left phrenic nerve. Similarly, testing may be done to locate the vagus nerve and to determine which group of electrodes in the electrode assemblies most effectively stimulate the vagus nerve.

This testing and nerve location may be controlled and/or monitored via control unit 14 or 14', which may include testing programming and/or applications. For example, control unit 14 or 14' may test the electrodes and electrode combinations to determine which combinations (e.g., bipolar, tripolar, quadrupolar, multipolar) of electrodes most effectively stimulate the targeted nerve, e.g., the right phrenic nerve, left phrenic nerve, and/or vagus nerve.

As a non-limiting example, testing could involve the use of a signal generator to systematically send electrical impulses to selected electrodes. By observing the patient's condition or by using sensors (either within or separate from the catheter), the desired stimulation electrodes may be identified. Electrodes may serve as both stimulating electrodes and as sensing electrodes, and the medical system may be integrated into a mechanical ventilator, which can be used to sense the patient's condition. Moreover, for example, the control unit may be programmed and/or activated to (a) select a first stimulation group of electrodes from the electrode assemblies to stimulate the left phrenic nerve, (b) select a second stimulation group of electrodes from the electrode assemblies to stimulate the right phrenic nerve, (c) select a third stimulation group of electrodes from the electrode assemblies to stimulate the vagus nerve (d) select a first stimulation current for the first stimulation group of electrodes to stimulate the left phrenic nerve, (e) select a second stimulation current for the second stimulation group of electrodes to stimulate the right phrenic nerve, and (f) select a third stimulation current for the third stimulation group of electrodes to stimulate the vagus nerve. The selection of electrodes and current levels may be preprogrammed or input based on the patient's characteristics, or the control unit may test different electrode groups and current levels and monitor the patient's response to determine the electrode pairs and current levels.

In some cases, the systems herein may include a transcutaneous noninvasive vagus nerve stimulator (nVNS) for stimulating a vagus nerve and/or a transcutaneous respiratory muscle stimulator. For example, devices that use electrical current from a small handheld or skin mounted device to stimulate a nerve in the neck or ear lobe may be used to stimulate a vagus nerve or stimulate nerves/muscles on the torso to activate a respiratory muscle. Alternatively or additionally, various other methods may be used to stimulate nerves, such as, for example, subcutaneous electrodes or nerve cuffs connected to the control unit.

When an electrical charge is delivered to the phrenic nerves, the diaphragm muscles may contract and generate negative pressure in the thoracic cavity. The lungs then expand to draw in a volume of air. This contraction of diaphragm muscles can be sensed manually by palpation or by placing a hand on the thoracic cavity, as shown in FIG. 2. Alternatively, the breathing activity can be sensed by placing an airflow or airway pressure sensor in the breathing circuit or placing sensors 16, such as accelerometers or a gyroscope, on the surface of the skin at the thoracic region, as shown in FIG. 2. Sensors 16 can be hard wired to control unit 18 or can be connected using wireless transmitters and receivers.

Figure 8:
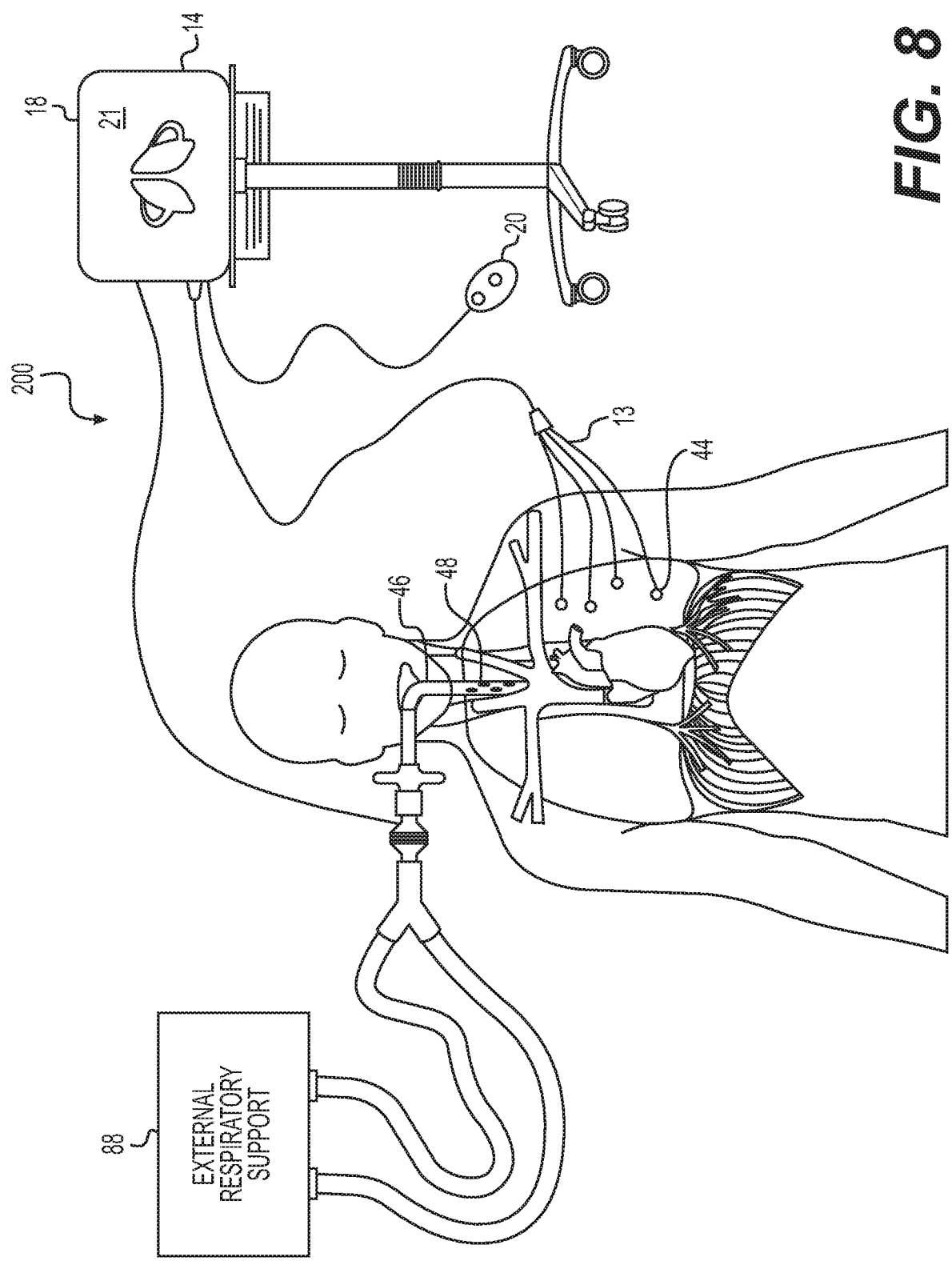
FIG. 8 illustrates the anatomy of respiratory muscles of the torso, a transdermal respiratory muscle stimulation array of electrodes placed upon the skin of the patient over the intercostal muscles, transesophageal stimulation electrodes, and an external respiratory support device, according to an exemplary embodiment.

FIG. 8 illustrates the anatomy of the neck and chest, similar to FIG. 1. FIG. 8 further illustrates an exemplary medical system 200 that includes a transcutaneous electrode array 13. The array 13 includes a series of electrodes 44 placed on the surface of the skin of the patient in close proximity to the intercostal muscles. Electrodes 44 may have any suitable shape and size, and may serve a variety of functions, such as sensing electrical activity and stimulating the muscles or nerves through the skin. Electrodes 44 can include stainless steel, conductive carbon fiber loaded ABS plastic, silver/silver chloride ionic compound, or any other suitable material, or any combination of materials. Each electrode 44 can be covered by a polymeric or elastomeric film that may include an adhesive to attach the electrode 44 to skin. Alternatively, the electrode film may contain electrolyte gel for better conduction of the signals. In some embodiments, other forms of electrodes, for example subcutaneous or needle electrodes, can be used to stimulate intercostal muscles, or the system may use other forms of stimulation energy, such as ultrasound, to activate the target nerves or muscles.

FIG. 8 further illustrates a transesophageal tube 46 with electrodes 48 on the tube (e.g., integrated on the tube) and/or on an inflatable balloon surrounding all or part of tube 46. Electrodes 48 can be printed on the surface of tube 46 (or the balloon) using conductive ink such as silver ink, gold ink, graphene ink, or carbon-based ink. Alternatively, electrodes 48 can be formed by using an adhesive to secure the electrode material, such as platinum iridium, stainless steel, titanium, or similar material, to tube 46 and connecting electrodes 48 to control unit 18 with one or more conductive wires. Electrodes 48 can be used to sense the signals from the phrenic nerves or vagus nerves or some other neurological element. Electrodes 48 can also be used to stimulate the nerves, such as, for example, at least one of vagus nerves, phrenic nerves, sympathetic ganglia, or the esophageal sphincter.

Alternatively or additionally, system 200 of FIG. 8 can include a catheter with electrodes and/or sensors, as described in the FIG. 2. To restore negative pressure ventilation, system 200 can stimulate one or both phrenic nerves to activate the diaphragm muscles, along with stimulating the intercostal muscles (as illustrated via electrodes 44), to create a negative pressure in the thoracic cavity or a compressive force to the chest cavity. The system may receive feedback by sensing the phrenic or vagus activity from one of the electrodes on the intravascular catheter (if used) or transesophageal tube 46. Feedback from nerve activity may be used to determine the stimulation parameters required to sustain proper ventilation and whether adjustments to the stimulation parameters are needed. The system can also receive feedback from any other suitable sensor to determine the appropriate stimulation parameters. One or more of each of the following sensors may be included in either system 100 or system 200: an airflow sensor, an airway pressure sensor, an accelerometer, a gyroscope, a blood gas sensor, or a sensor to detect an inflammatory agent. In some examples, system 100 or system 200 may include a sensor to detect an inflammatory agent. Examples of such inflammatory agents include, but are not limited to, erythrocyte sedimentation rate (ESR), cytokines, C-reactive protein (CRP), plasma viscosity (PV), hemoglobin A1C, serum ferritin, red blood cell width, insulin, nitric oxide, or other biomarkers for an inflammatory disease (e.g., inflammatory bowel disease, Alzheimers, Crohn's Disease, Arthritis, cancers, diabetes).

Figure 9:
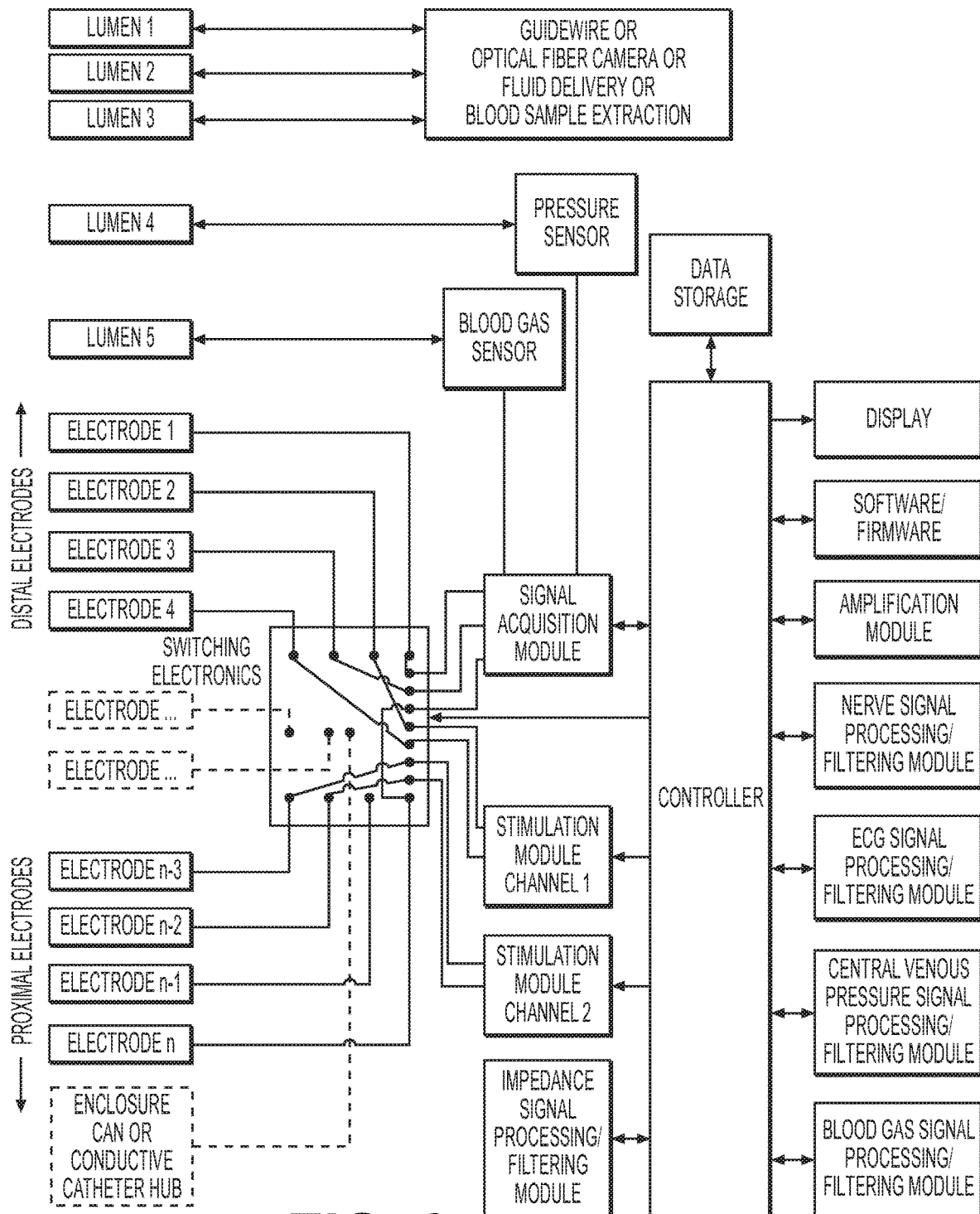
FIG. 9 illustrates a block diagram of a nerve stimulation system having an intravascular catheter and a control unit, according to an exemplary embodiment.

FIG. 9 illustrates a block diagram of the various components of system. The electrodes, hub, and lumens may be part of catheter described herein. The catheter may have any number of electrodes and any number of lumens. Five lumens are illustrated in FIG. 9, but in different examples, the catheter may include one, two, three, four, or more than five lumens. In one example, the catheter may have three lumens (e.g., extension lumens and corresponding internal lumens), which each may hold one or more of a guidewire or optical fiber camera or may be used for fluid delivery or blood sample extraction. In another example, the catheter may include four lumens, with one lumen holding or fluidly connected to a pressure sensor, one lumen holding or fluidly connected to a blood gas sensor, and the other two lumens holding a guidewire or optical fiber camera and/or being used for fluid delivery or blood sample extraction. It should be understood that any lumen of the system may contain or be fluidly connected to any of the devices (e.g., sensors, guidewire, optical fiber camera) described herein and/or may be used for any of the functions described herein (e.g., fluid delivery, blood sample extraction).

The system may include a controller, which may be part of any of the control units described herein. Each of the components of the system may be operably coupled to the controller, and the controller may manage operation of electrodes during nerve stimulation, control the gathering of information by various sensors and electrodes, and control fluid delivery or extraction. It should be understood that the various modules described herein may be part of a computing system and are separated in FIG. 9 for explanatory purposes only; it is not necessary for the modules to be physically separate.

The electrodes may be electronically coupled to switching electronics, which may be communicably coupled to the controller. As shown in FIG. 9, a portion of the electrodes may be distal electrodes, and a portion of the electrodes may be proximal electrodes. Some electrodes may be positioned on separate catheters. The hub also may be connected to switching electronics and may be used as an electrode.

The electrodes may be used for both electrically stimulating nerves and for gathering physiological information. When being used for nerve stimulation, a first combination of electrodes (e.g., one, two, three, or more electrodes) may be electrically coupled to a first stimulation module channel for stimulation of a first nerve (e.g., the right phrenic nerve) and a second combination of electrodes (e.g., one, two, three, or more electrodes) may be electrically coupled to a second stimulation module channel for stimulation of a second nerve (e.g., the vagus nerve). There may also be a third or fourth channel to stimulate more nerves or muscles. Electrical signals may be sent from the first and second stimulation module channels to the electrode combinations to cause the electrodes to stimulate the nerves. In other examples, more than two electrode combinations (e.g., 3, 4, or more) may be used to stimulate one or more target nerves, and the system may include more than two stimulation module channels.

The electrodes may be further configured to sense physiological information from a patient, such as nerve activity, ECG, or electrical impedance, as will be described further below. When being used for sensing, one or more of electrodes may be electronically coupled to a signal acquisition module. The signal acquisition module may receive signals from electrodes.

The switching electronics may selectively couple electrodes to first stimulation module channel, the second stimulation module channel, or the signal acquisition module. Switching electronics may change which electrodes are used for stimulation and which are used for sensing at any given time. In one example, any electrode can be used for nerve stimulation and any electrode can be used for sensing functions described herein. In other words, each electrode may be configured to stimulate nerves, and each electrode may be configured to sense physiological information.

The signal acquisition module may further be coupled to one or more sensors configured to gather physiological information from a patient. For example, the system may include one or more of a blood gas sensor or a pressure sensor. These sensors may be located in lumens of the catheter, outside of the patient in fluid communication with a lumen, on an outer surface of the catheter, or in any other suitable location. In one example, the blood gas sensor may be housed in or fluidly connected to a lumen, while the pressure sensor may be housed in or fluidly connected to another lumen. The blood gas sensor may measure the amount of $O_2$ or $CO_2$ in the patient's blood. The pressure sensor may measure the central venous pressure (CVP) of the patient.

The signal acquisition module may transmit the signals received from one or more of electrodes, the blood gas sensor, and/or the pressure sensor to the appropriate processing/filtering module of the system. For example, signals from the pressure sensor may be transmitted to a central venous pressure signal processing/filtering module, where the signals are processed and filtered to aid in interpretation of CVP information. Similarly, signals from the blood gas sensor may be transmitted to a blood gas signal processing/filtering module for processing and filtering to determine blood gas levels. Signals from electrodes, when they are used for sensing, may be sent to a nerve signal processing/filtering module, an ECG signal processing/filtering module, or an impedance signal processing/filtering module, as appropriate. Signals from electrodes or other sensors may be sent to an amplification module, if necessary, to amplify the signals prior to being sent to the appropriate processing/filtering module.

Exemplary Methods for Preventing or Treating Brain Injury

The systems and methods described herein may prevent, modulate, control, or treat brain injury while pacing the diaphragm. The brain injury may be caused by mechanical ventilation. The systems and methods may perform tests on a brain function and/or a status of vagus nerve stimulation. Based on the results of the tests, one or more phrenic nerves and/or vagus nerves may be stimulated. Stimulation of the nerves may reduce inflammation in the brain. Alternatively or additionally, one or more nerves (e.g., vagus) may be blocked using signals from electrodes to block aberrant signaling from the brain.

In one exemplary therapy session, catheter 12 may be positioned in the vasculature to extend adjacent or across the left and right phrenic nerves 26, 28. Appropriate distal and proximal electrode pairs may be selected to cause a contraction of the respiratory muscle, e.g., both the left and right hemi-diaphragm muscles. The operator (e.g., physician or patient) may set the stimulation pulse train length at about 1.2 seconds, a pulse amplitude to about 100% of a threshold value, and an initial pulse width to about 100% of a threshold value. Pulse parameters can be adjusted to achieve the desired level of muscle contraction and reduction in positive lung pressure from an external respiratory support device 88. The pulse width can be modulated between stimulation pulses in the stimulation pulse train. In some cases, the pulse amplitude can be modulated between stimulation pulses in the stimulation pulse train. Using the remote hand held controller 20, the operator may provide a therapy set of 10 stimulation pulse trains. In some examples, each of the stimulation pulse trains may be timed to coincide with a breath delivered by a mechanical ventilator or the patient's spontaneous breath.

In some embodiments, the system can communicate directly with a mechanical ventilator, or other external respiratory support system (e.g., external respiratory support 88), to coordinate the therapy delivery with the support provided by the external device. As previously described, sensors detecting activity from diaphragm muscles, nerves (e.g. phrenic nerves, vagus nerves, etc.) or other patient monitors or respiratory support devices can be used to trigger stimulation and/or breath delivery from a mechanical ventilator. Also, as a non-limiting example, the systems described herein may be operably connected (e.g., hardwired, wireless, etc.) to receive a signal from the mechanical ventilator indicating the initiation of a breath to the patient, and the systems can synchronize the delivery of the stimulation pulse train to coordinate with a desired phase of the breath. In another example, an operator may set the stimulation parameters and ask the patient to activate their breathing muscles. The operator may then coordinate the trigger of electrical stimulation with the patient efforts to provide maximum exercise of the muscles. In another example, external respiratory support 88 can be reduced or even eliminated during a portion of or all of the delivery of a stimulation set or stimulation session.

In some examples, 10 stimulations pulse trains are provided. The pulse trains can be timed to 10 sequential breaths, or the operator may skip one or more breaths to allow the patient to rest periodically between stimulations. After the 10 stimulation pulse trains are delivered, the patient may be allowed to rest for a period of time, for example 30 seconds to 5 minutes. After a suitable rest, the operator can initiate a second set, for example 10 breaths, again followed by a resting period. The operator can deliver several sets, e.g., 4 sets, that each includes 10 stimulations. Each stimulation may cause a muscle contraction, for a total of 40 muscle contractions over a 1- to 15-minute period. The desired number of stimulations for a session may be delivered in a single set, if needed. The patient may then be permitted to rest (e.g., for one or more hours), and in some cases at least 3 hours, and potentially as long as 24 or 48 hours before beginning another therapy session. In some instances, two to three, or more, therapy sessions are delivered each day. Regardless, the number of stimulations provided to the respiratory muscles may be a small fraction of the breaths required by the patient each day. In the previously-described example of 40 stimulations/day, the number of stimulations delivered is approximately less than 0.2% or about 0.2% of the breaths taken by or delivered to the patient per day.

In one example, the stimulation parameters may be kept the same from one stimulation that causes muscle contraction to the next stimulation, from one therapy set to the next therapy set, from one session to the next session, or from one day to the next day. In other examples, one of the parameters, such as the stimulation amplitude, the stimulation frequency, the stimulation hold time, or the resistance of the breathing circuit, may be increased or decreased between two stimulations that cause muscle contractions, between two sets, between two sessions, or between two days. The factors to consider while changing parameters may be patient tolerance, unintended stimulation of other structures, fatigue, or a desire for increased strength.

In another example of a therapy session, stimulation signals may be delivered over a total period of time of approximately 2 hours or less, during one or more therapy sessions during that total of 2 hours or less, during a 24-hour period. In another example, stimulation signals may be delivered over a total period of time of 5 hours or less during a 24-hour period.

In other examples of therapy sessions, stimulation signals may be delivered to contract one or more respiratory muscles for no more than: 20% of the breaths taken by or delivered to the patient in a 24-hour period; 10% of the breaths taken by or delivered to the patient in a 24-hour period; 2% of the breaths taken by or delivered to the patient in a 24-hour period; or 0.2% of the breaths taken by or delivered to the patient in a 24-hour period.

In another example, a brief stimulation therapy session lasting approximately 3 to 10 minutes may be delivered 12 to 24 times over a 24-hour period; 6 to 12 times over a 24-hour period; or once in a 24-hour period.

In another example, therapy sessions may be administered until the patient no longer requires external respiratory support; or up to 48 hours after the time at which the patient no longer requires, or is no longer receiving, external respiratory support.

Various examples of the subject disclosure may be implemented soon after the patient begins using external respiratory support (e.g., mechanical ventilation) to help reduce the loss of strength and or endurance of a respiratory muscle. Various examples of this disclosure can be used to help reduce the level of injury to a patient's lungs, heart, brain and/or other organs of the body. It is contemplated that a stimulation with every breath, or alternatively a majority of breaths, may provide a desired level of protection.

The systems described herein can be programmed to vary the profile of the stimulation pulse trains from time to time. For example, every tenth stimulation pulse train can be programmed to be longer than the others to produce a deeper or longer breath (e.g., sigh breath). In this case, the duration of the stimulation pulse train between two adjacent pulse trains will vary.

In some examples, therapy may be continued and steps related to activating the stimulator and ceasing activation of the stimulator may be repeated until MIP reaches a predetermined value.

Furthermore, steps of any therapy treatment described herein may be carried out with respect to more than one nerve and more than one respiratory muscle. Stimulations of multiple nerves (and one or more respiratory muscles) may be synchronized so that the patient's muscle or muscles are stimulated at the same time. To achieve this synchronization, two or more combinations of selected electrodes may be activated at the same time during a therapy session. For example, if the first set of electrodes emits electrical signals up to 100 times, the second set of electrodes may emit electrical signals up to 100 times, with each emission of the second set corresponding to an emission of the first set of electrodes. In one example, the first and second sets of electrodes may be used to stimulate the left and right phrenic nerves to cause synchronized contractions of the left and right hemi-diaphragms. In another example, the first set may be used to stimulate the diaphragm, and the second set may be used to stimulate the intercostal muscles. The diaphragm and the intercostal muscles may be stimulated simultaneously. Alternatively, the diaphragm and the intercostal muscles may be stimulated out of phase. For example, when the external intercostal muscles are stimulated, the diaphragm may be stimulated simultaneously with the external intercostal muscles. When the internal intercostal muscles are stimulated, the diaphragm and the internal intercostal muscles may be stimulated out of phase. Both stimulations may occur at the same time in the patient breath cycle. In yet another example, the patient's nerves/muscles may be stimulated during an inspiratory period of the patient's ventilator or other external respiratory support.

While most examples described herein consider that a therapy session will be delivered by a health care professional, other approaches of therapy delivery may be utilized that also deliver infrequent respiratory muscle stimulation to build strength. As a non-limiting example, a closed-loop automated example of the system of this disclosure can be designed to deliver a stimulation to a respiratory muscle at a specific duty cycle such as 1 stimulation for every X breaths, where X could range from 10 to 1000. This approach may provide for periodic muscle stimulation with a predetermined number of resting breaths in between. X may be as small as 1 and as large as 10,000 in various examples. When using the systems and methods described herein to prevent respiratory muscle atrophy as well as lung and brain injury, the stimulations can be provided more frequently, potentially as often as every breath.

Various electrodes may be used to stimulate nerves and/or muscles as described in this disclosure. As examples, the stimulators described herein may include one or more of: nerve stimulation electrodes, endotracheal electrodes, endoesophageal electrodes, intravascular electrodes, transcutaneous electrodes, intracutaneous electrodes, electromagnetic beam electrodes, balloon-type electrodes, basket-type electrodes, umbrella-type electrodes, tape-type electrodes, suction-type electrodes, screw-type electrodes, barb-type electrodes, bipolar electrodes, monopolar electrodes, metal electrodes, wire electrodes, patch electrodes, cuff electrodes, clip electrodes, needle electrodes, or probe electrodes. Furthermore, the stimulation energy may be delivered by an energy form that includes at least one of mechanical, electrical, ultrasonic, photonic, or electromagnetic energy.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

We claim:
1. A method for treating a subject, comprising:
   stimulating a first nerve with a first stimulation signal comprising an amount of a stimulation parameter, wherein the stimulation parameter includes a stimulation charge, a frequency of pulses within a stimulation train, or a breath rate, and wherein stimulation of the first nerve with the first stimulation signal assists or causes contraction of a respiratory muscle in the subject;
   while stimulating the first nerve, inhibiting transmission of an aberrant signal by a second nerve;
   ventilating a subject with a mechanical ventilator;
   imaging a brain in the subject, measuring a brain oxygenation in the subject, or measuring an intracranial pressure in the subject, wherein imaging the brain, measuring the brain oxygenation, or measuring the intracranial pressure provides a test result, and wherein the test result comprises an effect of ventilation on the brain, from the mechanical ventilator;
   comparing the test result to a predetermined value to determine a condition of the brain of the subject;
   modifying the amount of the stimulation parameter based on the test result; and
   stimulating the first nerve with a second stimulation signal comprising the modified amount of the stimulation parameter, wherein stimulation of the nerve with the second stimulation signal assists or causes contraction of the respiratory muscle in the subject.
2. The method of claim 1, wherein inhibiting transmission of the aberrant signal by the second nerve initiates a biological response in the brain that reduces a level of a causing factor of a brain injury.
3. The method of claim 1, wherein the second nerve is a vagus nerve.

4. The method of claim 1, wherein inhibiting the transmission of the aberrant signal includes inhibiting a signal from the second nerve to the brain or a lung in the subject.
5. The method of claim 1, wherein the transmission of the aberrant signal is inhibited by an electrical signal delivered by an external nerve stimulator.
6. The method of claim 5, wherein the external nerve stimulator is positioned on a skin area adjacent to a vagus nerve in the subject.
7. The method of claim 1, wherein the transmission of the aberrant signal is inhibited by an electrical signal delivered by an implantable nerve stimulator.
8. The method of claim 1, further comprising stimulating a third nerve.
9. The method of claim 8, wherein the first nerve is a left phrenic nerve, the second nerve is a vagus nerve, and the third nerve is a right phrenic nerve.
10. The method of claim 1, wherein the transmission of the aberrant signal is inhibited by manual, mechanical, electrical, ultrasonic, or electromagnetic energy.
11. The method of claim 1, comprising imaging the brain, wherein the test result includes an image generated by magnetic resonance imaging, a computed tomography scan, or a magnetoencephalography scan.
12. The method of claim 1, wherein the brain condition is determined based on a level of an inflammation- or pain-related protein in blood of the subject.
13. The method of claim 1, wherein the first nerve is a phrenic nerve, and the respiratory muscle is a diaphragm muscle.
14. The method of claim 1, wherein stimulating the nerve comprises inserting a catheter with one or more electrodes in a blood vessel of the subject, and positioning the one or more electrodes proximate the first nerve.
15. The method of claim 1, wherein inhibiting transmission of the aberrant signal by the second nerve occurs during at least a portion of a ventilation inspiration period.
16. The method of claim 1, wherein the test result is indicative of brain injury or dysfunction.
17. The method of claim 1, wherein inhibiting transmission of the aberrant signal by the second nerve includes reducing transmission of an aberrant signal by the second nerve.
18. A method for treating a subject, comprising:
   ventilating the subject with a mechanical ventilator;
   stimulating a phrenic nerve with a stimulator to assist or cause contraction of a respiratory muscle in the subject;
   quantifying vagus nerve activity in the subject, wherein the quantification of vagus nerve activity includes an effect of mechanical ventilation on the vagus nerve activity of the subject, and wherein the quantification of vagus nerve activity is obtained by testing heart blood flow, testing peripheral blood flow, testing blood pressure, imaging, or assessing inflammation or pain-related molecules in blood of the subject;
   generating a stimulation parameter based on the quantification of vagus nerve activity; and
   stimulating the phrenic nerve with a stimulation signal delivered from an electrode of the stimulator that is more proximate to the phrenic nerve than a vagus nerve, wherein the stimulation signal includes the stimulation parameter.
19. The method of claim 18, further comprising stimulating the vagus nerve based on the stimulation parameter.
20. The method of claim 18, further comprising comparing a test result generated from testing heart blood flow, testing peripheral blood flow, testing blood pressure, imaging, or assessing inflammation or pain-related molecules in blood of the subject to a threshold or a range, and wherein generating a stimulation parameter based on the quantification of vagus nerve activity includes determining a stimulation parameter based on the comparison of the test result to the threshold or the range.

21. The method of claim 18, wherein the quantification of vagus nerve activity is obtained by testing peripheral blood flow or imaging.

22. A method of treating a subject, the method comprising:
- stimulating a nerve with a first stimulation signal comprising an amount of a stimulation parameter, wherein the stimulation parameter includes a stimulation charge, a frequency of pulses within a stimulation train, or a breath rate, and wherein stimulation of the nerve with the first stimulation signal assists or causes contraction of a respiratory muscle in the subject;
- ventilating the subject with a mechanical ventilator; and
- performing a test that provides a test result, wherein the test result comprises an effect of ventilation on the brain from the mechanical ventilator;
- determining a condition of a brain in the subject by comparing the test result to a predetermined value or range;
- modifying the amount of the stimulation parameter based on the condition of the brain; and
- stimulating the nerve with a second stimulation signal comprising the modified amount of the stimulation parameter, wherein stimulation of the nerve with the second stimulation signal assists or causes contraction of the respiratory muscle in the subject.

23. The method of claim 22, wherein stimulating the nerve with the second stimulation signal includes stimulating a phrenic nerve and does not include stimulating a vagus nerve.

* * * * *